United States Patent [19]

Sung

[11] Patent Number: 4,885,254

[45] Date of Patent: Dec. 5, 1989

[54] FLUORESCENE TECHNIQUE TO MONITOR CURE IN POLYMERS

[75] Inventor: Chong S. P. Sung, Lexington,, Mass.

[73] Assignee: University of Connecticut, Storrs, Conn.

[21] Appl. No.: 132,567

[22] Filed: Dec. 11, 1987

Related U.S. Application Data

[63] Continuation-in-part of Ser. No. 878,138, Jun. 25, 1986, Pat. No. 4,717,674, which is a continuation-in-part of Ser. No. 800,443, Nov. 21, 1985, abandoned.

[51] Int. Cl.$^4$ ............................................. G01N 33/44
[52] U.S. Cl. ........................................ 436/85; 436/34; 436/56; 436/172; 436/903; 534/588; 534/689
[58] Field of Search ..................... 436/85, 34, 56, 172, 436/903, 173; 260/97, 102; 534/588, 689

[56] References Cited

U.S. PATENT DOCUMENTS 4,543,335 9/1985 Sommers et al. .................... 436/170
4,717,674 1/1988 Sung .................................. 436/172

OTHER PUBLICATIONS

I. J. Chin and C. S. P. Sung, *Macromolecules*, 17:2603–2607 (1984).
I. J. Chin and C. S. P. Sung, *Polymer Preprints*, 25(2):199–200 (1984).
C. S. P. Sung et al., *Polymer Preprints, 27(2): (1986)*.
C. S. P. Sung et al., *Macromolecules*, 19:2922–2932 (1986).
M. K. Antoon et al., *Polym. Comp.*, 2:81 (1981).
"Isothermal Cure Kinetics of an Epoxy Resin Prepreg" by G. L. Hagnauer et al., ACS Symp. Ser. 221, 229–244 (1983).
"SEC Analysis of Epoxy Resin Cure Kinetics", by G. L. Hagnauer et al., ACS Symp. Ser. 227, 25 (1983).
"Effects of Impurities on Hydrolytic Stability & Curing Behavior", by Hagnauer et al., ACS Symp. Ser. 221, 193–209 (1983).
"Microdielectrometry: A New Method for In Situ Cure Monitoring", by N. F. Sheppard et al., Proc. of the 26th SAMPE Symp., Los Angeles 65 (1981).
"Torsional Braid Analysis", by John B. Enns & John K. Gilliam, Am. Chem. Society, Advances in Chem. Series, #203, 1983, Ch. 2, 27–63 (1983).
"Some Molecular Motions in Epoxy Polymers: A C Solid–State NMR Study" by A. N. Garroway et al., *Macromolecules*, 15: 1051–1063 (1982).
"Studies of Epoxy Resin Systems: Part B", by T. D. Chang et al., *Polym. Eng. Sci.* 22:1213–1220 (1982).
Org. Coatings & App. Polym. Sci., Proc. (ACS), 48(1), 116–120 (1983) by R. L. Levy and D. P. Ames.
Wang et al., *ACS Polym. Mater. Sci. Eng. Prac.*, 49:138 (1983).
A. Gupta et al., *J. Appl. Polym. Sci.*, 28:1011 (1983).

(List continued on next page.)

*Primary Examiner*—David L. Lacey
*Assistant Examiner*—L. Johnson
*Attorney, Agent, or Firm*—Hamilton, Brook, Smith & Reynolds

[57] ABSTRACT

A method for determining the extent of polymerization of a polymer system consisting of adding a fluorescent label, the label having a reactivity similar to the reactivity of the curing agent, to the polymer system and measuring the fluorescence intensity proportional to cure species concentration during polymerization. The fluorescence intensity of the label exhibits sensitive changes throughout the polymerization process, allowing one to follow cure reactions in a quantitive way by measuring fluorescence, especially in the latter stages of cure. The cure species composition, reactivity ratio, activation energy and weight-average molecular weight can also be determined by adding a label and measuring the UV-VIS spectra in addition to the fluorescence intensity. Reaction of the label with the monomer produces spectrophotometric shifts which are deconvoluted based on the band assignments of model compounds to obtain compositional analyses of cure products.

19 Claims, 24 Drawing Sheets

OTHER PUBLICATIONS

"Nitroxide Spin Labeling of Epoxy Resins", by I. M. Brown & T. C. Sandreczki, *Macromolecules*, 16:1890–1895 (1983).

"Substitution Effects in Property Relations for Stepwise Polyfunctional Polymerization", by D. R. Miller, *Macromolecules*, 13:1063–1069 (1980).

"Curing of Epoxy Resins. I", by K. Dusek & M. Ilavsky, *J. Polym. Sci. Symp.*, 53:29–44 (1975).

"A New Derivation of Post Gel Properties of Network Polymers", by D. R. Miller et al., *Macromolecules*, 9:206–211 (1976).

"Structure of Diepoxide–Diamine Network Polymers. I.", by J. M. Charlesworth, *J. Polym. Phys.*, 17:1557–1569 (1979).

"A Critical Compilation of Substituent Constants", by N. B. Chapman and J. Shorter, *Correlation Analysis in Chemistry*, 457, Plenum Press, Burkus et al., *J. Am. Chem. Soc.*, 80:5948 (1958).

Barbalata et al., *European Polymer J.*, 14:427 (1978).

Ferstanding et al., *J. Am. Chem. Soc.*, 81:4838 (1959).

(DAA)  (GPE)

M.W.

1st Compound (362)

2nd Compound (512)

3rd Compound (512)

4th Compound (662)

5th Compound (812)

DGEBA-DDS-DAA

DGEB-DDS-DAA

KINETIC SCHEME OF EPOXY CURE REACTIONS

DGEBA

DGEBA

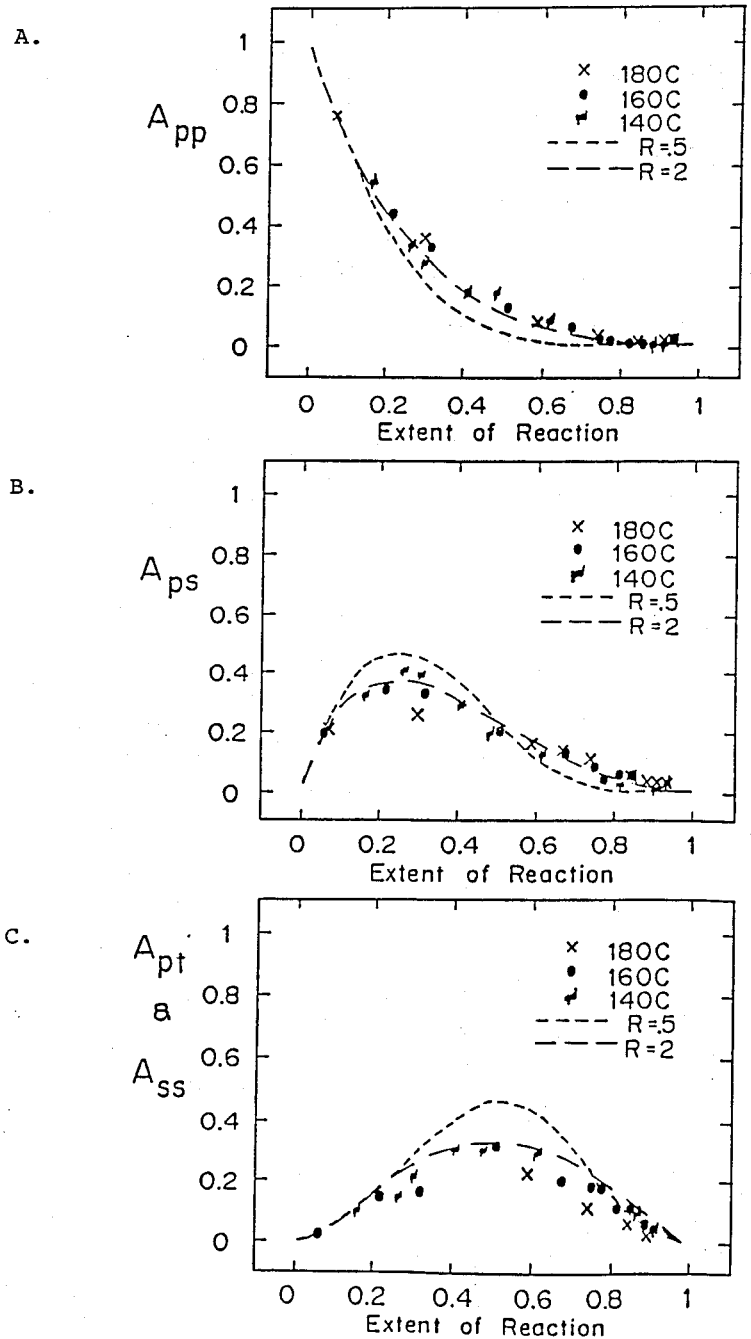

DGEB

D.

E.

FLUORESCENE TECHNIQUE TO MONITOR CURE IN POLYMERS

GOVERNMENT RIGHTS

The Government has rights in this invention by virtue of Grant No. DMR-82-05897 from the National Science Foundation, Polymers Program, Contract No. DL-H-225243 from C. S. Draper Laboratories, and Contract No. DAAG29-85-K-0055 from Army Research Office.

RELATED APPLICATIONS

This application is a continuation-in-part of allowed U.S. patent application Ser. No. 878,138 now U.S. Pat. No. 4,717,674 filed June 25, 1986 by Chong Sook Paik Sung entitled "Method to Characterize Curing of Epoxy with Aromatic Diamines" which is a continuation-in-part of abandoned U.S. patent application Ser. No. 800,443 filed Nov. 21, 1985, now abandoned, by Chong Sook Paik Sung and In-Joo Chin entitled "Method to Characterize Curing of Epoxy with Aromatic Diamines by Azochromophore Labelling", both teachings of which are incorporated herein by reference.

BACKGROUND OF THE INVENTION

This invention relates generally to a method of chemical analysis and particularly to a method for characterizing the curing of a polymer.

The structure and properties of polymers are known to strongly depend on the extent of cure and physical aging which has taken place after the cure cycle is completed. A number of physiochemical techniques have been used or developed toward a better characterization of cure and physical aging phenomena in epoxies, for example. Among them are such techniques as FT-IR spectroscopy described by M. K. Antoon et al. in *Polym. Comp.*, 2 81 (1981); thermal analyses described in G. L. Hagnauer et al. in *ASC Symp Ser.*, 221, 229 (1983); GPC (size exclusion chromatography), described by G. L. Hagnauer et al. in *ASC Symp Ser.*, 227, 25 (1983) and Ser., *ASC Symp Ser.*, 221, 193 (1983); microdielectrometry, described by N. F. Sheppard et al. in *Proc. of the 26th SAMPE Symposium*, Los Angeles, 65, (1981); torsional braid analyses described by J. B. Enns et al. in *ASC Symp Ser.*, 203, 27–63 (1983); $^{13}C$ solid-state NMR, described by A. N. Garroway et al. in *Marcomolecules*, 15, 1051 (1982); thermally stimulated current measurement, described by T. D. Chang et al in *Polym. Eng. Sci.*, 22, 1213 (1982); fluorescence, described in R. L. Levy et al. in *ASC Org. Coat. Appl Polym. Sci. Proc.*, 48, 116 (1983) and Wang et al in *ACS Polym. Mater. Sci. Eng. Proc.*, 49, 138 (1983); and ESR spectroscopy, described by A. Gupta et al. in *J. Appl. Polym. Sci.*, 28, 1011 (1983).

While these techniques provide useful information on the extent of cure and on epoxy structure, there are certain limitations and disadvantages associated with each technique. For example, FT-IR fails to monitor later stages of cure when the epoxy peak disappears. The use of GPC and of size exclusion chromatography is limited to the early stages of the curing reaction. The fluorescence techniques measure the emission of the epoxy as a function of increasing viscosity, not the formation of reaction products. ESR techniques also primarily measure decreasing mobilities of the label with increasing cure and viscosity but provide only limited information on the reaction products. For example, Brown and Sandreczki in *Macromolecules*, 16, 1890 (1983) observed different ESR spectra which may allow spectroscopic monitoring of the initial addition products of the reaction of an epoxy with a nitroxide monoamine, if the reactivity of the nitroxide is similar to that of a diamine.

$^{13}C$ MAS-CP (magic angle spinning-cross polarized) solid-state NMR is another technique for the characterization of polymeric solids. As Garroway et al demonstrated in *Macromolecules*, 15, 1051 (1982), it can provide information on certain molecular motions in epoxy. It is not easy, however, to obtain quantitative compositional information on the reaction products by $^{13}C$ NMR in cross-linked polymers due to such complications as line broadening and spinning side bands. The fact that the peak intensity is not generally representative of the concentration in crosspolarization experiments is another problem. $^{15}N$ NMR, in principle, may be more useful, but its sensitivity is poor because of the low natural abundance.

Abandoned application, U.S. Ser. No. 800,443 entitled "Method to Characterize Curing of Epoxy with Aromatic Diamines by Azochromophore Labelling", filed Nov. 21, 1985, described a new method to obtain quantitative compositional information on the curing of epoxy with aromatic diamines by azochromophore labelling. In this technique, a small amount of azochromophore, such as p,p'-diaminoazobenzene (DAA), which has reactivity similar to the curing agent, such as diaminodiphenyl sulfone (DDS), is used to provide an indication of the extent of cure. As the epoxy is cured, $\lambda_{max}$ of the $\pi \rightarrow \pi^*$ transition corresponding to the azo bond of the curing agent is red-shifted in a way that provides spectral discrimination for the cure products (crosslinkers, branch points, linear chains, chain ends and unreacted diamines). The accuracy of the compositional analyses depends on the proper assignments of $\lambda_{max}$ positions and the determination of the extinction coefficients for the various cure products.

The allowed application, U.S. Ser. No. 878,138, entitled "Method to Characterize Curing of Epoxy with Aromatic Diamines", filed June 25, 1986, describes a new method to obtain quantitative compositional information on the curing of epoxy by monitoring the fluorescence intensity of azochromophore labels contained in the reaction mixture. The fluorescence intensity of the azochromophore labels was found to have a characteristic variation with the composition of the epoxy system reaction mixture, thereby allowing fluorescence intensity to be used to perform a highly accurate compositional determination.

Epoxies formed with aromatic diamines such as DGEBA-DDA (diglycidyl ether of bisphenol A-diaminodiphenyl sulfone) are important for high-temperature applications. In the DGEBA-DDS system, at the stoichiometric ratio, there are five major species during curing. This is because the amine groups are the major reactive species, and the hydroxyl groups do not initiate epoxy-polymerization in uncatalyzed epoxy cured with aromatic diamines at the stoichiometric ratio.

In order to understand cure mechanism, kinetics, and structure/property correlations, it is important to know the relative concentrations of the primary reaction products during the course of the curing process.

A need still exists for a means for determining the extent of cure in applications utilizing epoxies and other polymers of varying thickness and in particular on metallic substrates in situ.

Furthermore, it would be highly desirable to provide a process for determining the relative concentrations of the primary reaction products produced during the curing of polymers.

Further, a need exists for a sensitive method for determining the reactivity ratios, the activation energy, and the weight-average molecular weight of the reaction products produced during the polymerization of various polymers.

SUMMARY OF THE INVENTION

The present invention is a method, and labelled polymer system for use in the method, for monitoring polymerization of various polymer systems. The invention is based on the discovery that polymers labelled with an azobenzene dye, an azonaphthalene dye, a benzylidene-dianiline dye, a stilbene dye or diamines of highly conjugated aromatic compounds exhibit very sensitive changes in fluorescence intensity corresponding to emission by the label as a function of cure extent. The label should be selected to have a reactivity similar to that of the curing agent. As shown by the following examples using different polymer systems, fluorescence intensity at the label increases sharply during curing allowing for sensitive cure monitoring during the later stages of cure.

By combining this method with the method of monitoring the relative composition of cure products utilizing the deconvolution of the UV-VIS spectra during polymerization of the polymer system, parameters characteristic of cure kinetics and mechanisms such as cure product composition, reactivity ratio of primary versus secondary cure products, initial rate constants and activation energy can be obtained.

DETAILED DESCRIPTION OF THE INVENTION

Figure 1:
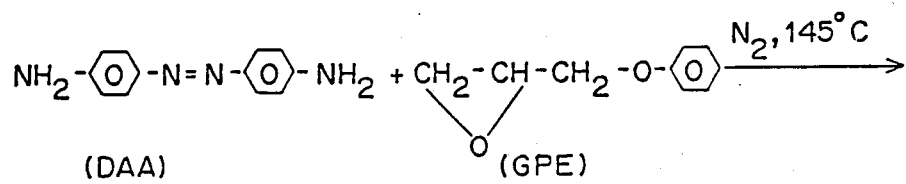
FIG. 1 is the chemical structures of the major model compounds expected from the reaction of DAA and GPE at 145° C. under $N_2$ with a varying excess of GPE.
Figure 1:
Figure 1:
Figure 1:
Figure 1:
Figure 1:
Figure 1:
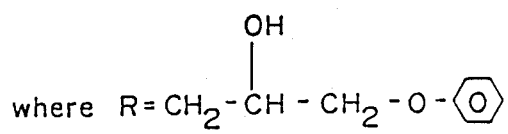

Fluorescence due to a chromophore label in various polymer systems increases sharply due to the increasing fluorescence quantum yield of cure products containing tertiary amines. Fluorescnce intensity is therefore used to determine the extent of cure, as well as to estimate composition, based on kinetic differential equations. UV-VIS spectral deconvolution can also be used to determine cure extent.

The method of determining the extent of curing of a polymer system by adding a chromophore label to the system and measuring the fluorescence intensity is applicable to any multifunctional polymer system. The chromophore label should be selected to have a reactivity similar to the reactivity of the polymer curing agent. Fluorescence is determined at the emission maximum of the chromophore label.

In examples utilizing DGEBA-DDS, diglycidyl ether of butane diol-diamino-diphenyl sulfone (DGEB-DDS) and DGEB-MDA epoxy systems labelled with DAA or DAS, PAA polyimide systems labelled with diamino naphthalene (DAN), and polyurea/polyurethane systems labelled with naphthalene diisocyanate (NDI), fluorescence was used to determine relative composition of cure products, the extent of cure, or for composition with the theoretically predicted weight average molecular weight and soluble fractions. UV-VIS and IR techniques were also used to determine the extent of cure in the polymer systems. Analysis of the UV-VIS spectra and the fluorescence spectra allows one to determine the cure product composition, reactivity ratio of primary amine versus secondary amines, initial rate constants and activation energy. Since IR and thermal analyses of the epoxy system suggested that DAA reacts a little faster than DDS, a calibration curve is constructed to correct for differences in the reactivities between the label and the curing agent.

Epoxy networks studied included DGEBA-DDS, DGEB-DDS, and diglycidyl ether of butane diol-methylene dianiline, (DGEB-MDA) epoxy. The first epoxy, DGEBA epoxy (diglycidyl ether of bisphenol A) has a maximum $T_g$ of 215° C. which leads to a complete cure, subject to degradation. When cured below 215° C., vitrification occurs some time after gelation (e.g., 150 minutes at a cure temperature of 160° C.) according to its T-T-T diagram. Since there is little progress in the cure reaction after vitrification, the extent of cure is limited. The second epoxy, DGEB epoxy (diglycidyl ether of butane diol), has a maximum $T_g$ of about 80° C. The cure reaction of DGEB can progress much further at cure temperatures above 80° C. due to the absence of vitrification.

The polymerization of these epoxy systems were characterized as follows, although such characterization is not required to practice the method of determining the extent of cure by measuring the fluorescence intensity of the chromophore label. First, the quantitative composition of each product over a wide range of cure extents were obtained for each of the epoxy networks cured at three isothermal temperatures. The reactivity ratio of the primary amine and the secondary amine with the epoxy group were then determined from this experimental data. The reactivity ratio is predicted to have a strong effect on the cure process including parameters such as gel time, molecular weight and the elastically active network chains. The activation energy is estimated from the initial slopes of the rate constants of the epoxy-primary amine reaction. The data are then compared assuming the weight average molecular weight as a function of cure using Miller and Macosko's recursive theory for network, described in *Macromolecules*, 13, 1063 (1980). Predicted soluble fractions are also compared with the composition of cure products.

The total fluorescence intensity by the DAA or DAS label at its emission maximum increases sharply as the cure proceeds. This behavior of DAA is not due to the viscosity change, but rather to the increasing fluorescence by the cure products. For DAS, fluorescence increase is due to viscosity as well as the cure reactions. The observed fluorescence intensities per mole of the model compounds representing each cure product in the DGEB-DAA and DGEB-DAA epoxy system are in the following ratios when excited at 456 nm: crosslinker (1400): branch point (1100): linear chain (18): chain end (9): DAA (1). Assuming the above ratios and using the known concentration of each cure product by deconvolution of UV-VIS spectra, the observed overall fluorescence intensity can be modeled as the sum of contributions from each cure product. Thus, fluorescence can be used to monitor cure reactions in DAA labelled epoxy.

In the following examples, the extent of cure of DGEBA-DDA, DGEB-DDA and DGEB-DDS epoxy was determined by the fluorescence method. Using the ratio of the amine functionality estimated from UV-VIS data, the composition of cure products at a given fluorescence intensity value were also estimated. The results are compared with those obtained by UV-VIS spectral deconvolution, as described in the abandoned application, U.S. Ser. No. 800,443, filed Nov. 21, 1985.

EXAMPLE OF CHARACTERIZING THE POLYMERIZATION OF DGEBA-DDS AND DGEB-DDS LABELLED WITH DAA

1. Synthesis of model compounds for determination of the quantitative composition over a wide range of cure extents p,p'-Diamino azobenzene (DAA) from Eastman Kodak Chemical, Rochester, NY was purified by passing it through basic alumina columns. This method of purification leaves little residue in a TLC plate in comparison to DAA recrystallized from toluene and acetone. Purified DAA has a melting point in the range of 238° C. to 241° C. 1,2-Epoxy-3-phenoxypropane (glycidyl phenyl ether, GPE) from Aldrich Chemical Co., Milwaukee, WI was used without further purification.

Model compounds were made by reacting DAA and GPE at 145° C. under $N_2$ with a varying excess of GPE. FIG. 1 shows the chemical structures of the major model compounds expected from this reaction. In order to obtain intermediate cure products, DAA and GPE were reacted in 1:4 molar ratio for 10 or 30 minutes at 145° C. After the reaction products were developed with a mixture of benzene:acetone:diethyl amine (16:3:1) five times, three well-separated spots in a TLC plate were seen. The top spot corresponds to DAA and the two lower spots (Fraction A and B) were purified and their properties summarized in Table 1.

In order to obtain products of the later stages of the reaction, DAA was reacted with a large excess of GPE (6,8, or 30 fold excess) for periods up to 4 hours at 150° C. under $N_2$. The major reaction products (Fraction C and D) appeared between Fraction A and B after developing 4 times with 13:1:1 mixture of benzene:acetone:diethylamine. The reaction mixture was initially fractionated by flash chromatography using silica gel at a pressure of 25 lbs/in² with the same solvent mixture described above. Out of the total fractions collected from flash chromatography, mother liquids of fractions 11 to 19 were combined after adding a 1:1 mixture of petroleum ether and ethanol to precipitate an orange powder. Preparatory TLC was used to separate Fraction C and D from this mother liquid by the same solvent mixture after developing 8 times. Their physical characteristics are also summarized in Table I.

TABLE I

Physical Characteristics of the Fractions Obtained by Reaction of DAA and GPE

| Fraction | Color | M.P. | Mass Spec | Nitrogen (cal'd/obs) | UV-VIS/um |
|---|---|---|---|---|---|
| A | Brown | <70° C. | m.w. 362 obs. | 15.46/13.79 | 420 |
| B | Reddish | 185-6° C. | m.w. 512 obs. | 10.93/10.75 | 445 |
| C | Yellowish | 177° C. | m.w. 662 (small peak) | not enough for analysis | 458 |

TABLE I-continued

Physical Characteristics of the Fractions Obtained by Reaction of DAA and GPE

| Fraction | Color | M.P. | Mass Spec | Nitrogen (cal'd/obs) | UV-VIS/um |
|---|---|---|---|---|---|
| D | Orange | 172° C. | obs. not available | 6.39/6.49 | 460 |

*Calculated based on the assumption that the Fraction A, B, and D correspond to the Model compounds 1, 2, (or 3) and 5, respectively.

**The main $\lambda_{max}$ is indicated while there were shoulders present in some fractions. The extinction coefficient at the main peak was approximately $4 \times 10^4$ moles/cm, independent of the fractions.

Fractions A, B, C and D obtained from model reactions were further analyzed by reverse phase HPLC using a Waters Associates, Milford, MA analytical system interfaced with a Spectra Physics data system. Reverse phase (Bondapak $C_{18}$) columns were employed, using a solvent programmer gradient and a varying amount of acetonitrile in water. An ultraviolet detector set at 280 nm was used.

2. Cure composition from analysis of the UV-VIS spectra

DGEBA was recrystallized from saturated methyl ethyl ketone solution by seeding it with purified DGEBA crystals and leaving it in the freezer ($-15°$ C.) for one to two weeks. DAA was recrystallized from toluene and acetone. DDS and DGEB were purchased from Aldrich and used without purification.

In typical cure monitoring studies, a small amount of DAA (approximately 5 to 7 mg or about 0.1% by weight for UV-VIS studies and 0.01% by weight in most fluorescence studies) was mixed with a stoichiometric mixture of DGEBA (5.0 g) or DGEB (2.98 g). DDS (1.825 g) was then added and the mixture heated with a magnetic stirrer at 120° C. for 5 minutes. Two circular quartz plates were clamped together with two thin Mular films (1.5 mil) on the edges leaving a center space for sample. The clamped quartz plate with Mylar spaces were dipped into epoxy heated to 100° C. The sample enters the center space by capiliary action.

UV-VIS spectra and fluorescence spectra were measured after curing the epoxy in an oven for a specific time and cooling the sample to room temperature. Fluorescence was measured with a 1 nm wide excitation slit and a 10 nm wide emission slit using a Perkin-Elmer MPF-66 spectrometer with a Model 7500 Data Station. UV-VIS spectra were obtained with a Perkin-Elmer Diode Array (Model 3840) System with a Model 7500 Data Station. The area under the UV-VIS peak was used to calibrate for concentration and thickness changes during cure to obtain the relative fluorescence intensity. UV-VIS spectra were deconvoluted with a computer program assuming a Gaussian distribution curve for each cure species. The $\lambda_{max}$'s of the various cure products were asigned 410, 420, 445, 460 and 470 nm, respectively.

The model compounds were analyzed as follows: Table 1 shows the physical characteristics of Model Compounds, Fractions A to D, which were purified by thin layer chromatography after reactions of DAA and GPE (in various excess) at 145° C. under $N_2$. There is a distinct color change as the fractions change from A to D. Fraction A is brownish as is DAA itself, while Fraction B is reddish. Fractions C and D are yellow and orange, respectively. Results of nitrogen analyses are close to the calculated results assuming that Fraction A, B or D corresponds to the Model compound 1, 2 or 5, respectively, as shown in FIG. 1. The UV-VIS spectrum shows shoulders in addition to the main absorption peak.

In order to ascertain if Fractions A to D are pure, reverse phase high pressure liquid chromatography using mixtures of acetonitrile and water as the mobile phase was carried out. A starting gradient of acetonitrile:water of 50:50 was used. DAA appears at 3.52 (76%) while GPE appears at 3.80. Fraction A shows a main peak at 5.72 (91%) and several small impurity peaks (<2% each). Fraction B shows its main peak at 7.26 (95%). Fraction C shows four peaks between 7 and 9, with two major peaks at 7.80 (68%) and 8.48 (16%). Fraction D shows a main peak at 7.20 (81%) and a small peak at 8.44 (7%).

While Fractions A and B are relatively pure, Fractions C and D are certainly mixtures. Closely-overlapping peaks for Fractions C and D were spread out by using a different starting gradient (80/20 ratio of acetonitrile to water). After the major peak was separated, the UV-VIS scan was taken in the HPLC instrument by switching the UV-VIS detector to the scanning mode. The maximum absorption for the major peak for the Fractions C and D is about 460 nm and 470 nm, respectively. For Fractions A and B, the absorption maxima were 420 nm and 445 nm, respectively. Since Fraction B is quite pure, it could be either model compound 2 or 3. These $\lambda_{max}$ positions, as summarized in Table II, were used in the deconvolution of the peaks obtained in the epoxy system. The extinction coefficient of about $4 \times 10^5$ mole/cm was measured regardless of the fractions so that an equal extinction coefficient was assumed in the deconvolution of the curves.

TABLE II

Positions of $\lambda_{max}$ max for Model Compounds of DAA and GPE

| Model Compound | $\lambda_{max}$ (nm) | $\Delta\lambda$ |
|---|---|---|
| DAA/(PP) | 410 | 0 |
| 1st (PS) | 420 | 10 |
| 2nd (SS) | 445 | 35 |
| 3rd (PT) | | |
| 4th (ST) | 460 | 50 |
| 5th (TT) | 470 | 60 |

*refer to FIG. 1 for chemical structure. Designation in parenthesis: P is primary amine, S is secondary amine and T is tertiary amine.

Figure 2A:
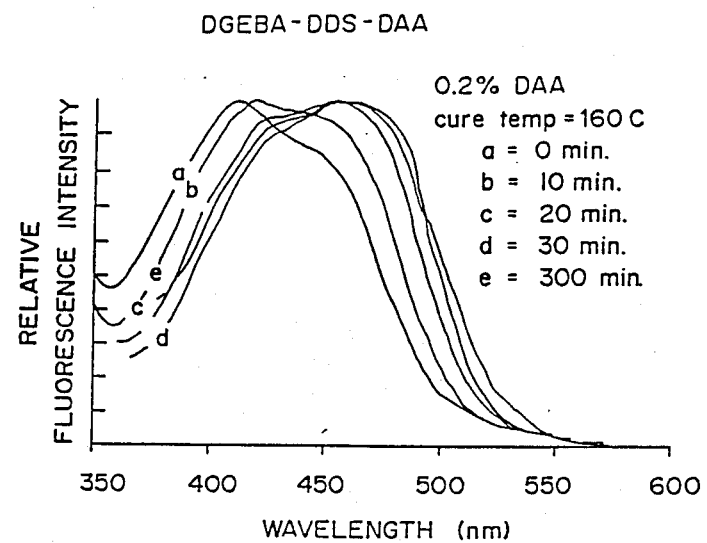
FIG. 2 is the UV-VIS spectra of p,p'-diaminoazobenzene (DAA) in a stoichiometric mixture of DGEBA-DDA (FIG. 2a) or DGEB-DDS (FIG. 2b) as a function of cure time at 160° C.
Figure 2B:
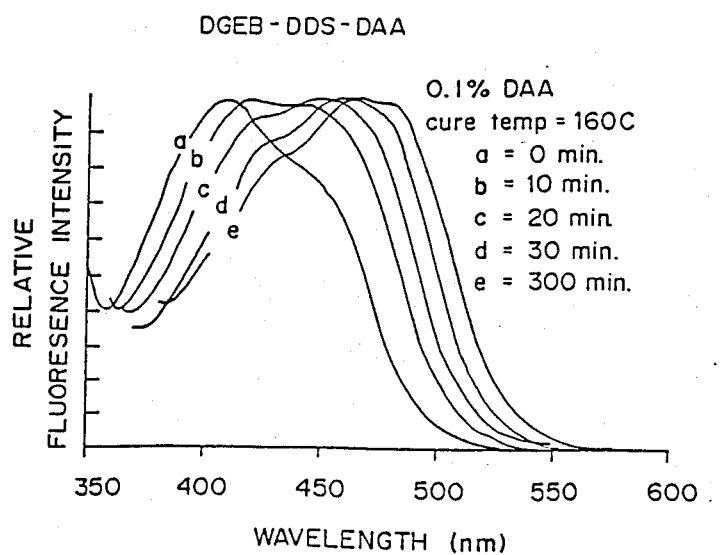

FIG. 2 compares UV-VIS spectra obtained as a function of cure time in DGEBA-DDS (FIG. 2a) and DGEB-DDS (FIG. 2b) at 160° C. In both sets of spectra, significant red shifts are observed with increasing cure time. In DGEBA-DDS epoxy, the matrix gels after about 50 minutes of cure and vitrifies after 150 minutes of cure. The cure reaction is quenched after vitrification. As a consequence, UV-VIS spectra in DGEBA-DDS matrix does not show much change after vitrification, as shown by "e" FIG. 2a corresponding to 300 min. cure time. In contrast, no vitrification occurs at 160° C. in DGEB-DDS epoxy since its maximum $T_g$ is only about 80° C. The cure reaction for the DGEB-DDS epoxy has been pushed further, as indicated by additional red shifts shown in "e" of FIG. 2b.

In order to insure that these spectral shifts are due to cure reactions and not to changes in the matrix (e.g., polarity change as a function of cure), UV-VIS spectra of the model compound representing cross-linkers in DGEBA-DDS epoxy were run as a function of cure at 160° C. Any spectral shift in this case would be due to the matrix change since the cross-linkers cannot react any further. Only a negligible (<5 nm) spectral shift was observed. The spectral shifts obtained in DAA labelled epoxy were therefore interpreted as arising from cure reactions only.

Table III summarizes the results on the composition of cure products by deconvolution of UV-VIS spectra with a computer program by assuming $_{max}$ positions of the model cure products according to Table II and a Gaussian distribution curve for each species. The error in resolving closely overlapping peaks in the spectra can be significant, especially when the cure is intermediate, for example, as with "b" and "c" in FIGS. 2a and 2b, however, the curve is fitted until the overall error calculated by the program is below two percent. The error in the composition of each cure product can still be as large as several percent, since the composition, given in Table III, corresponding to a certain cure time may not be an unique solution to the particular spectrum.

Figure 3:
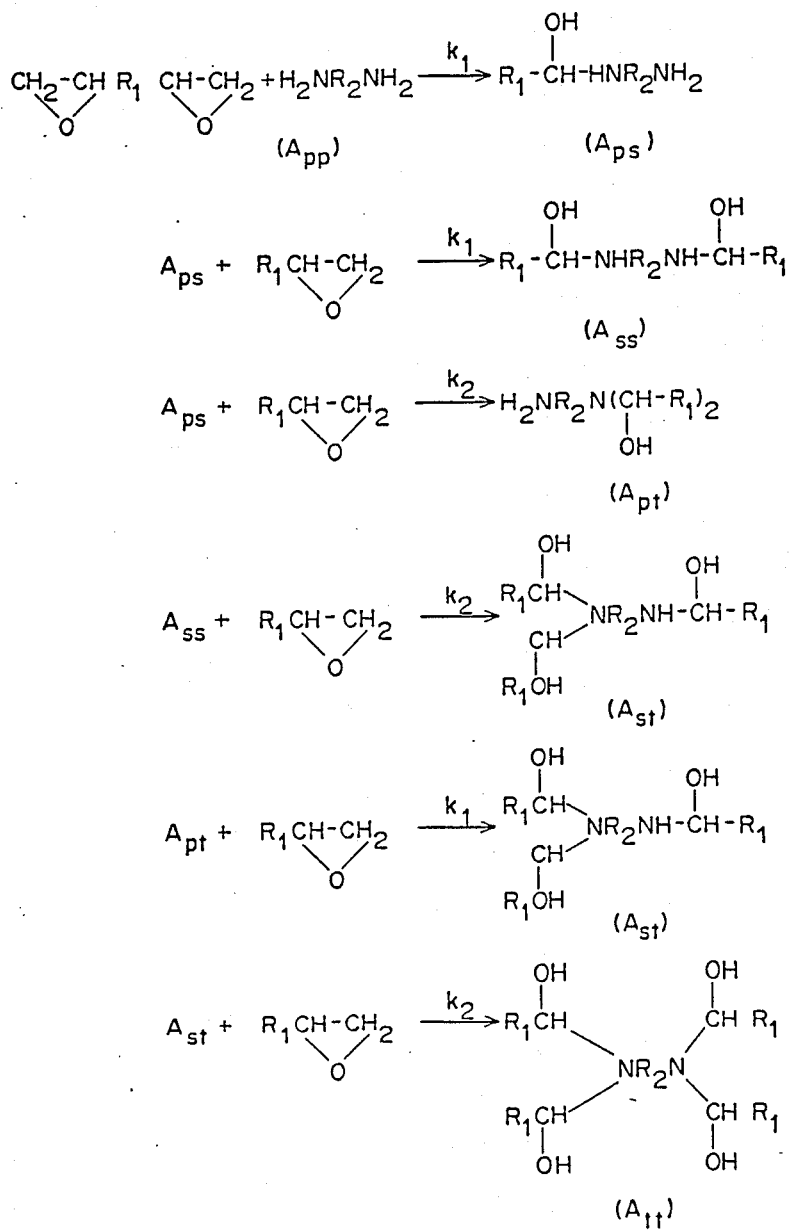
FIG. 3 is the kinetic scheme of the epoxy cure reactions, including the various cure products.

The computer program used in these examples is presented in application U.S. Ser. No. 878,138, filed June 25, 1986, which has previously been incorporated by reference. Similar programs for deconvolution of the spectra are commercially available.

cure products are shown in FIG. 3. $A_{pp}$ is the fraction of unreacted diamine.

As demonstrated by Table III: the fractions of branch points and cross-linkers increase with cure time for both epoxy matrices, as predicted by the spectral shifts of FIG. 2, and the cure reaction for DGEBA-DDS epoxy seems somewhat slower than DGEB-DDS, especially at long cure times, as shown by the values of the cure products as well as by comparing the overall extent of amine reaction ($\xi_a$) versus cure time (minutes) for both epoxy systems DGEB-DDS and DGEBA-DDS when cured at 160° C. In DGEBA-DDS, the maximum $\xi_a$ is only about 70%, presumably due to quenching by vitrification. Even in DGEB-DDS where vitrification does not occur at the cure temperatures, $\xi_a$ only reaches about 85% at this temperature.

The extent of amine cure for both epoxy systems is temperature dependent, as shown by a graph of $\xi_a$ versus time of curing (minutes) at 140° C., 160° C. and 180° C. At early stages of the cure, the effect of higher temperature is quite pronounced, leading to greater cure extent. However, at later stages of cure, the temperature does not have much effect, especially for DGEBA epoxy, leading to a plateau in the overall extent of reaction. This phenomenon is undoubtedly due to the vitrification occurring in DGEBA epoxy in comparison to the absence of vitrification in DGEB epoxy. The maximum $\xi_a$ obtained for DGEB-DDS when cured at 180° C. is about 95%.

3. Analysis of the cure kinetics and mechanisms

Since epoxy homopolymerization may be neglected in the absence of catalysts, the major cure reactions can be assumed to be the reactions between epoxide and amine groups, as shown in FIG. 3. The kinetic scheme

TABLE III

Composition of Cure Products in DGEB-DDS and DGEBA-DDS Epoxy as a Function of Cure Time at 160° C.

| Epoxy | Cure Time (min.) | $A_{pp}$ | $A_{PS}$ | $A_{SS} + A_{PT}$ | $A_{ST}$ | $A_{TT}$ | Extent of Amine Reaction ($\xi_a$) |
|---|---|---|---|---|---|---|---|
| DEGB-DDS | 0 | 78 | 20 | 2 | 0 | 0 | .059 |
| | 5 | 44 | 34 | 14 | 6 | 2 | .219 |
| | 10 | 33 | 33 | 16 | 11 | 7 | .318 |
| | 20 | 13 | 20 | 32 | 22 | 14 | .510 |
| | 30 | 6 | 12 | 20 | 31 | 31 | .676 |
| | 45 | 2 | 8 | 18 | 33 | 40 | .750 |
| | 70 | 2 | 4 | 17 | 36 | 41 | .775 |
| | 100 | 1 | 5 | 13 | 30 | 52 | .815 |
| | 150 | 1 | 5 | 11 | 21 | 62 | .848 |
| | 300 | 1 | 3 | 10 | 37 | 47 | .814 |
| | 800 | 1 | 3 | 13 | 34 | 49 | .813 |
| DEGBA-DDS | 0 | 75 | 25 | 0 | 0 | 0 | .063 |
| | 5 | 61 | 20 | 9 | 6 | 5 | .183 |
| | 10 | 35 | 41 | 9 | 9 | 5 | .270 |
| | 15 | 25 | 28 | 36 | 5 | 5 | .343 |
| | 30 | 10 | 17 | 17 | 23 | 34 | .636 |
| | 45 | 8 | 10 | 23 | 25 | 33 | .653 |
| | 60 | 9 | 15 | 19 | 25 | 33 | .646 |
| | 100 | 10 | 15 | 26 | 25 | 23 | .667 |
| | 150 | 10 | 15 | 15 | 29 | 27 | .675 |
| | 300 | 8 | 14 | 23 | 29 | 27 | .638 |
| | 140 | 7 | 20 | 12 | 20 | 42 | .680 |

The last column of Table III lists the extent of amine reaction ($\xi_a$) as defined by the following equation:

$$\xi_a = [A_{ps} + 2(A_{ss} + A_{pt}) + 3A_{st} + 4A_{tt}]/4 \quad (1)$$

where $A_{ps}$, $A_{ss}$, $A_{st}$ or $A_{tt}$ corresponds to the fractional amount of cure products, namely chain ends, linear chains, branch points or cross-linkers, respectively. The defines the rate constant $k_1$ as due to the conversion of primary amine to the secondary amine while $k_2$ is due to the conversion of secondary amine to the tertiary amine.

Based on FIG. 3, one can write a series of kinetic differential equations, as described by Dusek et al. in *J. Polym. Sci.*, Symp. No. 53, 29 (1975), as follows:

$$-\frac{d[pp]}{dt} = 4k_1[pp][b] \quad (2)$$

$$-\frac{d[ps]}{dt} = 2k_1[ps][b] + k_2[ps][b] - 4k_1[pp][b] \quad (3)$$

$$-\frac{d[ss]}{dt} = 2k_2[ss][b] - 2k_1[ps][b] \quad (4)$$

$$-\frac{d[pt]}{dt} = 2k_1[pt][b] - k_2[ps][b] \quad (5)$$

$$-\frac{d[st]}{dt} = k_2[st][b] - 2k_2[ss][b] - 2k_1[pt][b] \quad (6)$$

$$-\frac{d[tt]}{dt} = k_2[st][b] \quad (7)$$

where [b] is the concentration of unreacted epoxy groups.

Solving the above equations, one can obtain the fraction of each cure species only as a function of the reactivity ratio of $k_2/k_1$ and the fraction of unreacted diamine ($A_{pp}$):

$$A_{ps} = 2p(A_{pp}^q - A_{pp}) \quad (8)$$

$$A_{ss} = p^2(-2A_{pp}^q + A_{pp} + A_{pp}^{r/2}) \quad (9)$$

$$A_{pt} = -2pA_{pp}^q + rpA_{pp} + 2A_{pp}^{1/2} \quad (10)$$

$$A_{st} = p^2[(r+2)A_{pp}^q - rA_{pp} - \quad (11)$$
$$(2-r)A_{pp}^{1/2} - 2A_{pp}r/2 + (2-r)A_{pp}r/4]$$

$$A_{tt} = p^2\left[rA_{pp}^q + (r^2/4)A_{pp} + (r/p)A_{pp}^{1/2} + \quad (12)\right.$$
$$\left. A_{pp}^{r/2} - (2-r)A_{pp}^{r/4} + \left(\frac{r}{2}-1\right)2\right]$$

where $r = k_2/k_1$, $p = 1/(1 - r/2)$ and $q = (1 + r/2)2$

The overall extent of amine reaction ($\xi_a$) written in terms of App and r only, is as follows:

$$\xi_a = 1 - [1/(2-r)][(1-r)A_{pp}^{\frac{1}{2}} + A_{pp}^{r/4}] \quad (13)$$

Figure 4A:
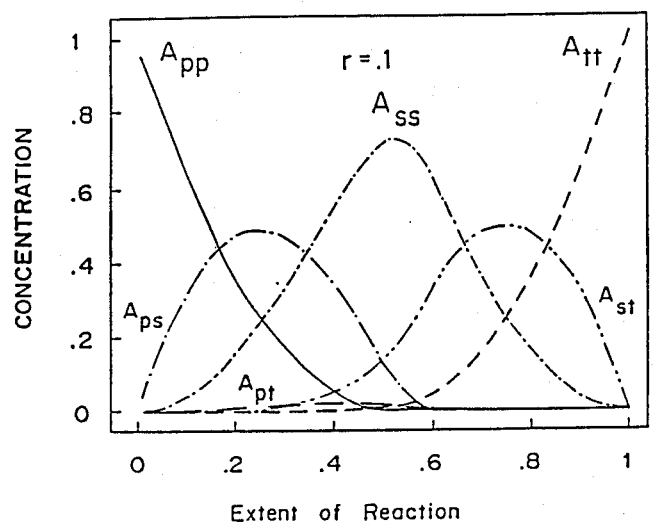
FIG. 4 is a graph of the theoretical composition of cure species as a function of amine reaction ($\xi_a$) according to equations 8-12 for reactivity ratios of 0.1 (FIG. 4a) and 2 (FIG. 4b).
Figure 4B:
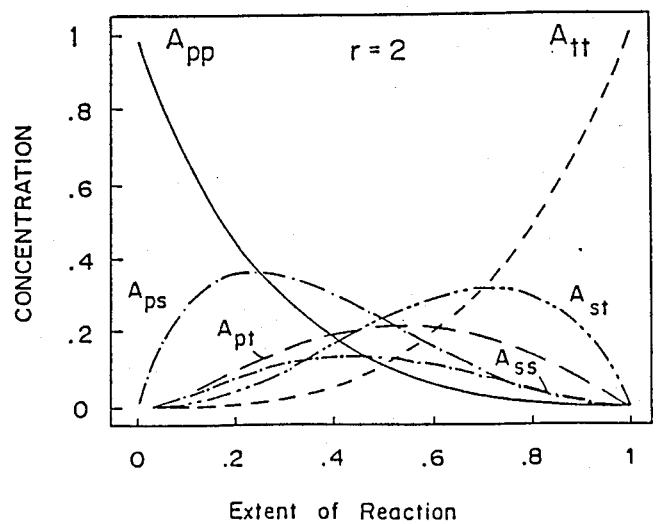

A calculated fraction of each cure product and of the unreacted diamine is plotted as a function of $\xi_a$, as shown in FIG. 4. The reactivity ratio, r, is assumed to be 0.1 in FIG. 4(a) and 2 in FIG. 4(b). Comparing these two figures, it becomes obvious that the smaller the r value, the greater the magnitude of $A_{ps}$, $A_{ss}$ and $A_{st}$. When r=2, $A_{pt}$ becomes noticable while it is negligible when r is less than one. At smaller value of r, $A_{pp}$ also decreases faster while $A_{tt}$ increases slower than at greater value of r.

Figure 5:
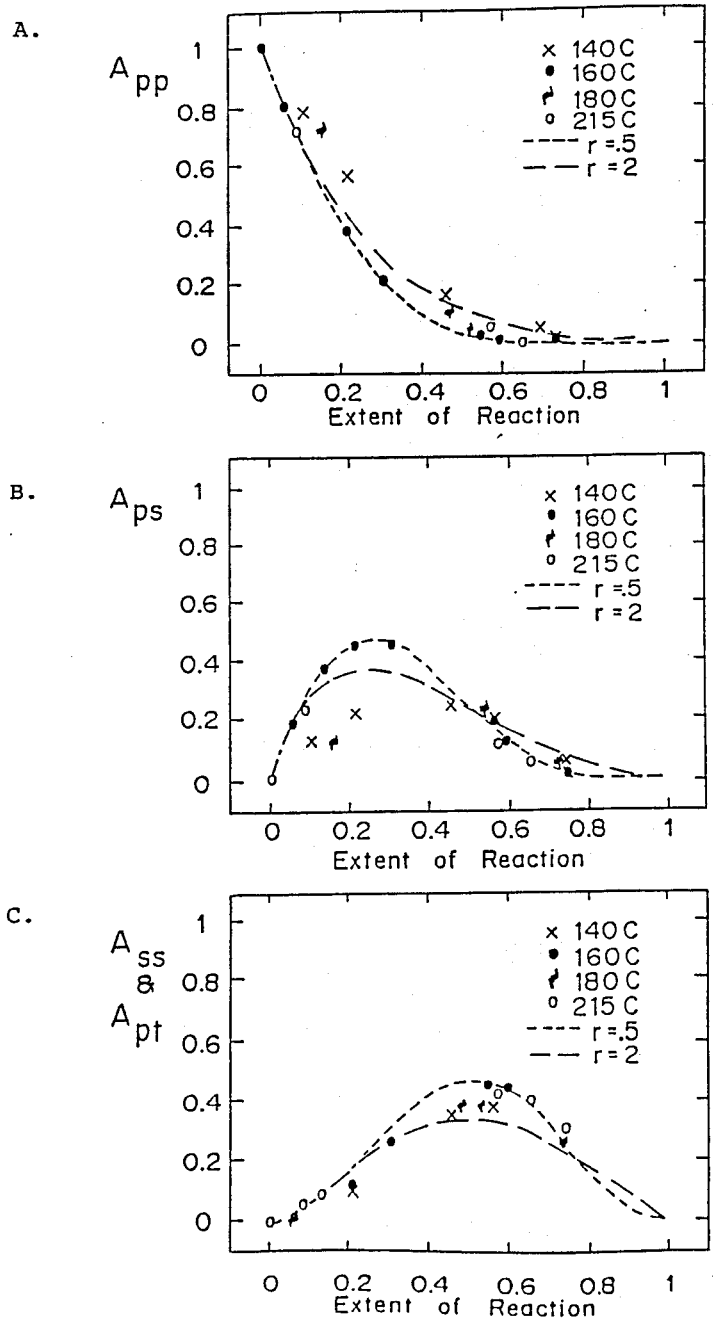
FIG. 5 and 5' are graphs of the experimental composition of cure species as a function of extent of amine reaction of DGEBA-DDS (FIG. 5) and DGEB-DDS (FIG. 5'), combining data from several cure temperatures.
Figure 5:
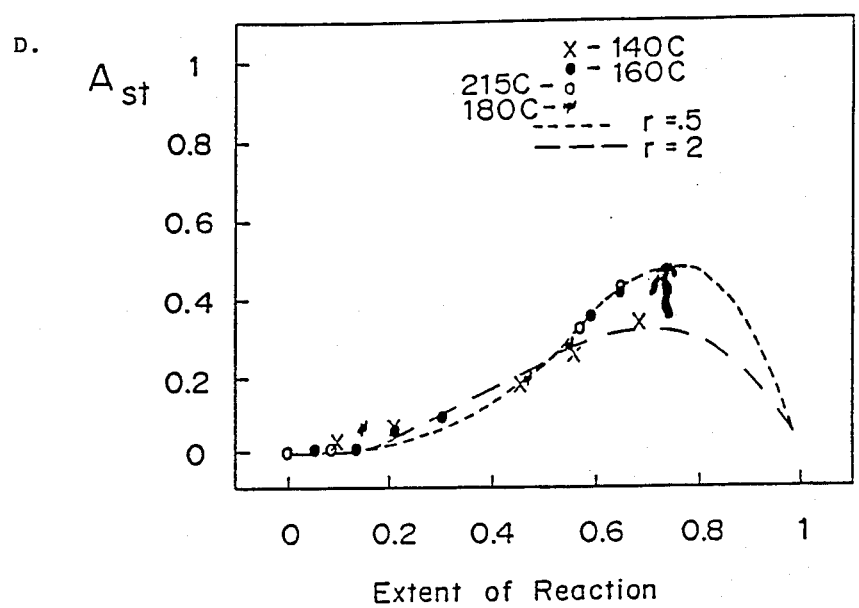
Figure 5:
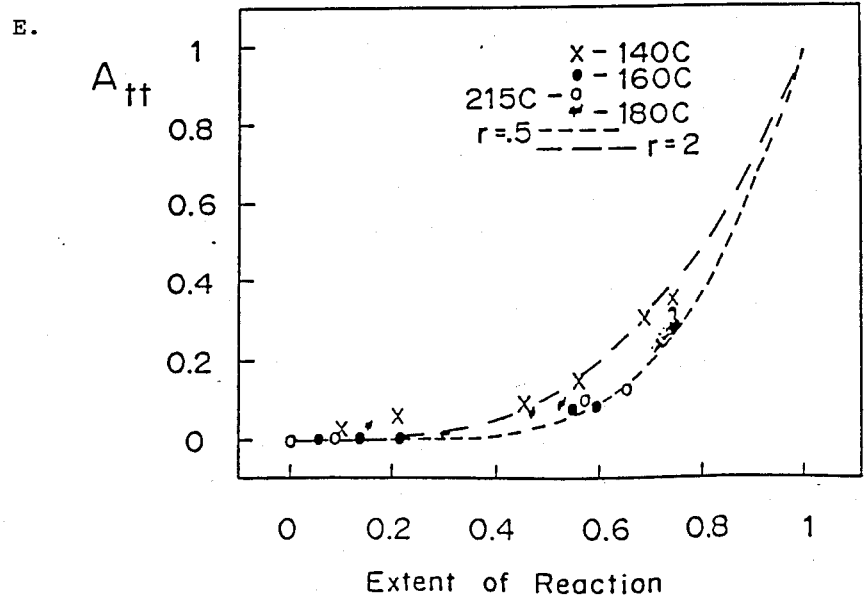
Figure 5:
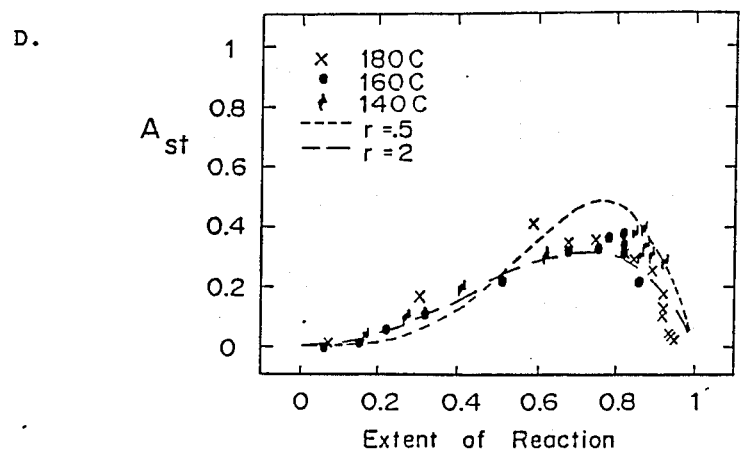
Figure 5:
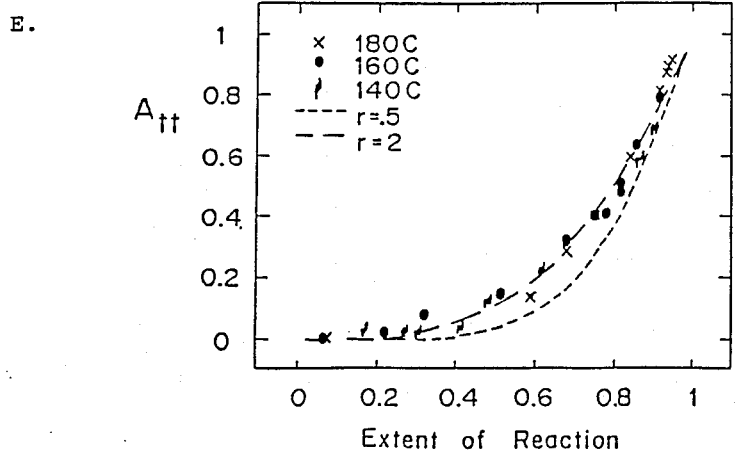

The r value has a strong effect on many structural parameters of the epoxy network. The fraction of each cure product is deconvoluted from the UV-VIS spectra obtained at three cure temperatures (140°, 160° and 180° C.) and plotted as a function of the extent of amine reaction in FIGS. 5 and 5'. As shown in FIG. 5, experimental data are only available up to about 75% reaction due to vitrification occurring in DGEBA-DDS epoxy. In contrast, experimental data are available up to 95% reaction in DGEB-DDS epoxy. Comparing the theoretical prediction of the composition of cure species as a function of amine reaction according to equations 8-12 for a reactivity ratio of 0.1 with the experimental composition of cure species as a function of extent of amine reaction, shown in FIGS. 5 and 5', allows one to determine the best fit r, or reactivity ratio to be used to deconvolute the spectra. The theoretical curves according to the equations 8-12, corresponding to r of 0.5 or 2, are plotted. The r value which seems to describe the experimental points best, in view of the range of experimental error, is then determined. As demonstrated, this is a r value close to unity. Thus, reaction rates of primary amine-epoxy and secondary amine-epoxy are practically indistinguishable in this system.

$k_1$ is then calculated from the kinetic equation (2). In order to integrate Eqn. (2), [b] (concentration of unreacted epoxy) and [$A_{pp}$] are expressed in terms of $\xi_a$.

By definition $$1 - \xi_b = \left[\frac{b}{4}\right]$$

Rearranging, the above equation becomes $$[b] = 4 - 4\xi_b \quad (14)$$

In a stoichiometric mixture, $\xi_a = \xi_b$. For the case of r=1, Eqn. (13) is reduced to $$\xi_a = 1 - [A_{pp}]^{\frac{1}{4}} \quad (15)$$

Rearranging Eqn. (15) leads to $$[A_{pp}] = (1 - \xi_a)^4 \quad (16)$$

Substituting Eqns. (14) and (16) into Eqn (2), $$\frac{-d(1-\xi_a)^4}{dt} = 16 k_1 (1-\xi_a)^5 \quad (17)$$

Rearrangement of Eqn. (17) leads to $$\frac{d\xi_a}{(1-\xi_a)^2} = 4k_1 dt \quad (18)$$

integrating $$\frac{\xi_a}{-(\xi_a - 1)} = -4k_1 t \quad (19)$$

Plotting $\xi_a/(\xi_a-1)$ versus time for DGEBA-DDS epoxy at three cure temperatures demonstrates that at cure times beyond gelation, the reaction rate constant which is proportional to the slope of these curves is clearly reduced. By drawing a straight line through the first few data points for the slope, $k_1$ is estimated to be $5.4 \times 10^{-3}$, $1.3 \times 10^{-2}$ and $3.1 \times 10^{-2}$ min$^{-1}$ at 140° C., 160° C., and 180° C., respectively.

An activation energy of 15.7 Kcal/mole and a pre-exponential factor of $1.2 \times 10^6$ min$^{-1}$ were estimated from an Arrehenius plot combining the data for both epoxy matrices.

4. Fluorescence Studies

The inherent fluorescence of the epoxy matrix itself is not useful to monitor cure reactions, as shown by the following: When excited at around 320 nm, both DGEBA-DDS and DGEB-DDS are highly fluorescent with an emission maximum around 370 to 380 nm. However, when the fluorescence intensity is calibrated for thickness fluctuations, the fluorescence intensity is constant with the extent of cure.

Figure 6A:
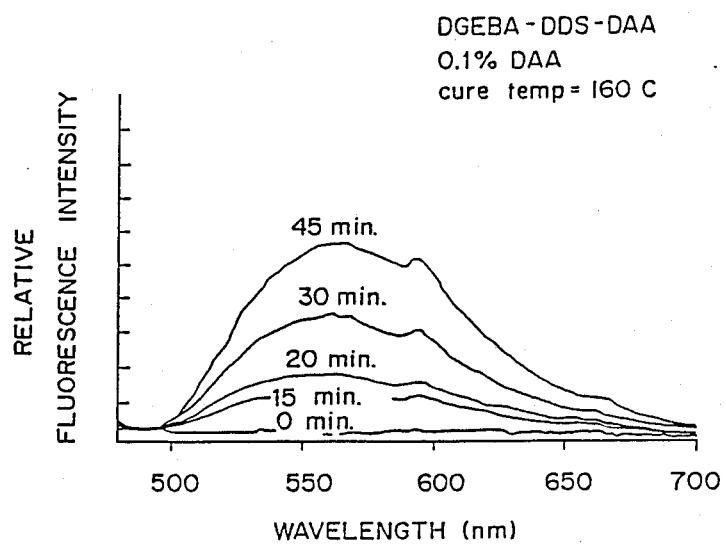
FIG. 6 is the fluorescence spectra of p,p'-diaminozaobenzene in a stoichiometric mixture of DGEBA-DDS (FIG. 6a) and DGEB-DDS (FIG. 6b) as a function of cure time at 160° C. (excitation at 456 nm).
Figure 6B:
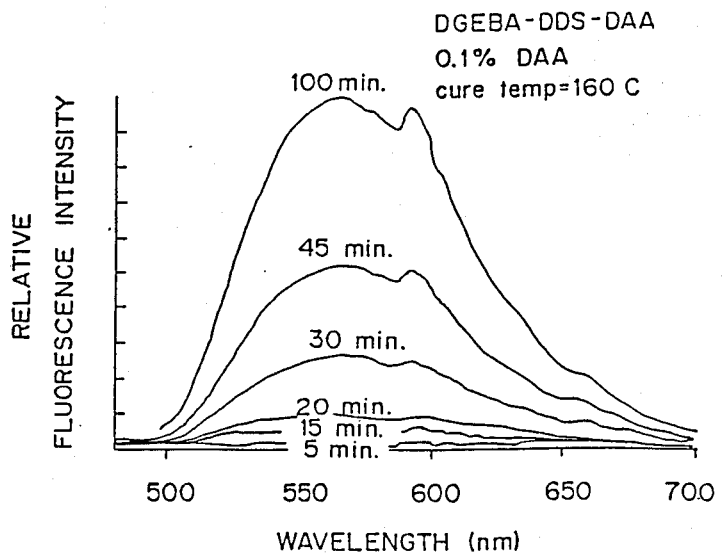
Figure 7:
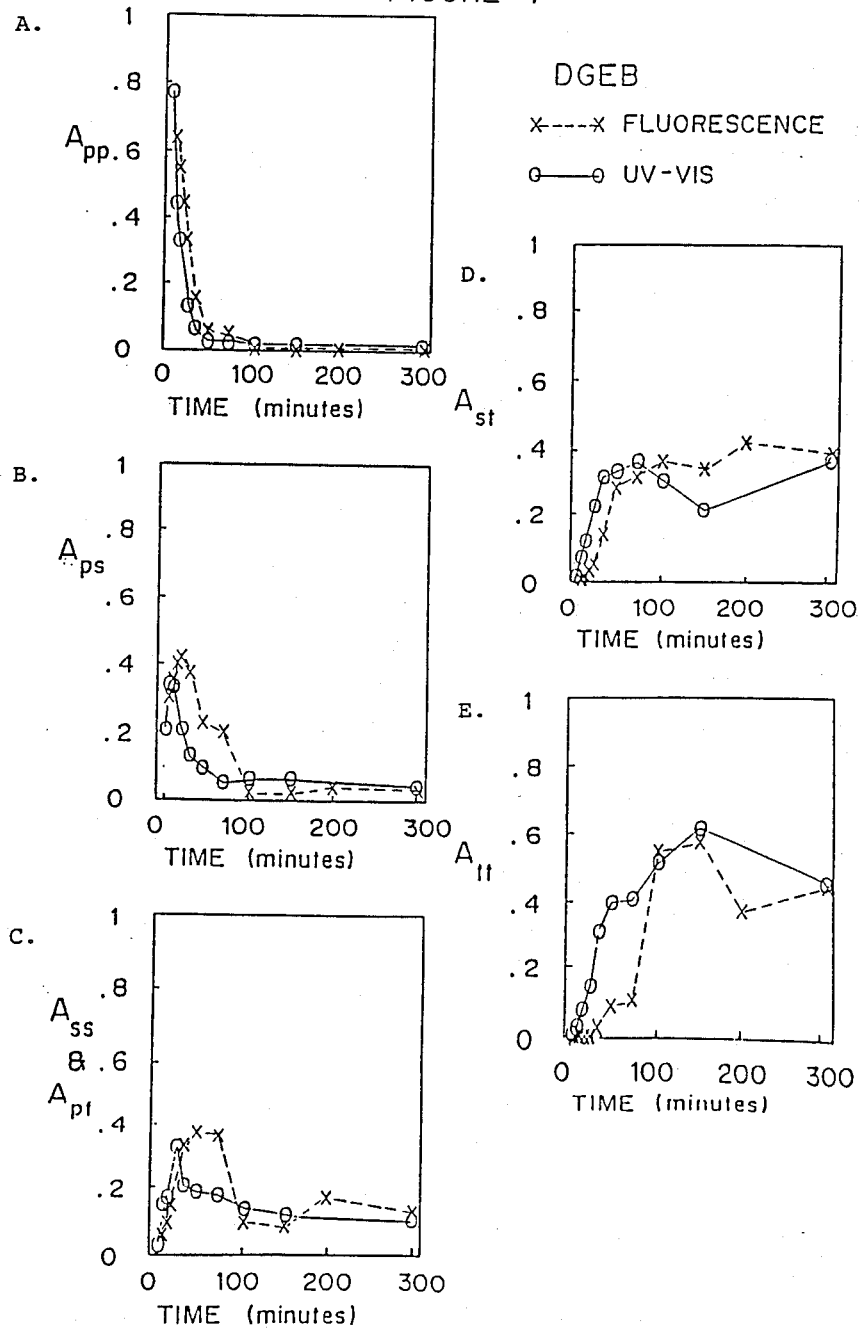
FIG. 7A-7E is a comparison of the cure compositions by UV-VIS deconvolution and by fluoroescence intensity.

In contrast, when the DAA label is excited, for example at 456 nm, a strongly cure dependent behavior of fluorescence intensity is observed. FIGS. 6a and 6b shows such fluorescence spectra for DGEBA-DDS-DAA and DGEB-DDS-DSS epoxy matrices respectively in the spectral range of 450 nm to 800 nm. In both epoxy matrices, at zero cure time, hardly any fluorescence is observed. But with increasing cure time, fluorescence with a broad emission peak seems to have red-shifted slightly, by 5 to 10 nm. This small red shift is in sharp contrast to much larger red shifts observed in UV-VIS spectra, shown in FIGS. 2a and 2b. Changes in polarity in the solvent medium is known to cause large shifts in emission spectra. Therefore, one can conclude that polarity did not change much as the epoxy cured. This trend was also suggested by small shifts in UV-VIS spectra by the model compound representing a cross-linker.

In order to quantify the fluorescence intensity changes, relative fluorescence intensity at 560 nm (after dividing by the UV-VIS peak area of the label) is plotted as a function of cure time at three cure temperatures for both epoxies. Fluorescence intensity for DGEB epoxy is about the same as for DGEBA epoxy up to gelation time. However, fluorescence increases continuously beyond gelation for DGEB but levels off in DGEBA epoxy, but not in DGEB epoxy. In DGEBA epoxy, the increase in fluorescence originates from the cure products alone rather than from the viscosity changes. Thus the total fluorescence intensity can be written as $I_F = c\Sigma F_i A_i$ where $F_i$ is the florescence intensity ratio obtained for each cure product under the same experimental conditions, $A_i$ is their concentration and $c$ is the experimental constant. The fluorescence intensity ratio for the cross-linker model compound is found to be independent of cure. Using the concentration values obtained by deconvolution of UV-VIS spectra, shown in Table III, the predicted $I_F$ agrees well with the experimental points. Much greater values of $I_F$ for DGEB are thus a direct consequence of further cure reactions, as also indicated by UV-VIS results as well as by IR monitoring of epoxy ring disappearance.

The extent of cure reaction is estimated from the fluorescence intensity values. As described before, the total fluorescence intensity is attributed to by the fluorescence of each cure product.

$$I_F = C(F_{pp}A_{pp} + F_{ps}A_{ps} + F_{ss}A_{ss} + F_{pt}A_{pt} + F_{st}A_{st} + F_{tt}A_{tt}) \quad (20)$$

From the model compound studies, the following fluorescence intensity ratio was estimated.

$$F_{pp}:F_{ps}:F_{ss}:F_{pt}:F_{st}:F_{tt} = 1:9:18:700:1100:1400 \quad (21)$$

Thus $$I_F = c(A_{pp} + 9A_{ps} + 18A_{ss} + 700A_{pt} + 1100A_{st} + 1400A_{tt}) \quad (22)$$

Substituting $A_{ps}$, $A_{ss}$, $A_{pt}$, $A_{st}$ and $A_{tt}$ by $A_{pp}$ and the amine reactivity ratio, r, according to Eqns (8–12), one obtains $$I_f = c\ (A_{pp} + 18p(A_{pp}^q - A_{pp}) +$$

$$18p^2(-2A_{pp}^q + A_{pp} + A_{pp}^{r/2}) +$$

(22)

-continued $$700(-2pA_{pp}^q + rpA_{pp} + 2A_{pp}^{1/2}) + 1100p^2[(r+2)A - q_{pp} -$$

$$rA_{pp} - (2-r)A_{pp}^{1/2} - 2A_{pp}^{r/2} + (2-r)A_{pp}^{r/4}] +$$

$$1400p^2[-rA_{pp}^q + (r^2/4)A_{pp} + (r/p)A_{pp}^{1/2} + A_{pp}^{r/2} -$$

$$(2-r)A_{pp}^{r/4} + (r/2 - 1)^2]$$

Eqn. (22) shows that $I_F$ is a function of only $A_{pp}$ for a given r. Using r=1 as determined from the extensive data in the previous section, and the experimental constant c, estimated from a few sets of known compositions to be on the order of 0.01, $A_{pp}$ is determined for a given $I_F$ using Eqn. (22).

Once $A_{pp}$ values are calculated, the concentration of other cure products can be calculated according to Eqn. (8–12). FIGS. 7A–7E shows a graphical representation of the data in comparison to the results obtained by UV-VIS deconvolution. As can be seen, the cure composition obtained from fluorescence is in reasonable agreement with the data obtained by deconvolution to UV-visible spectra.

Figure 8:
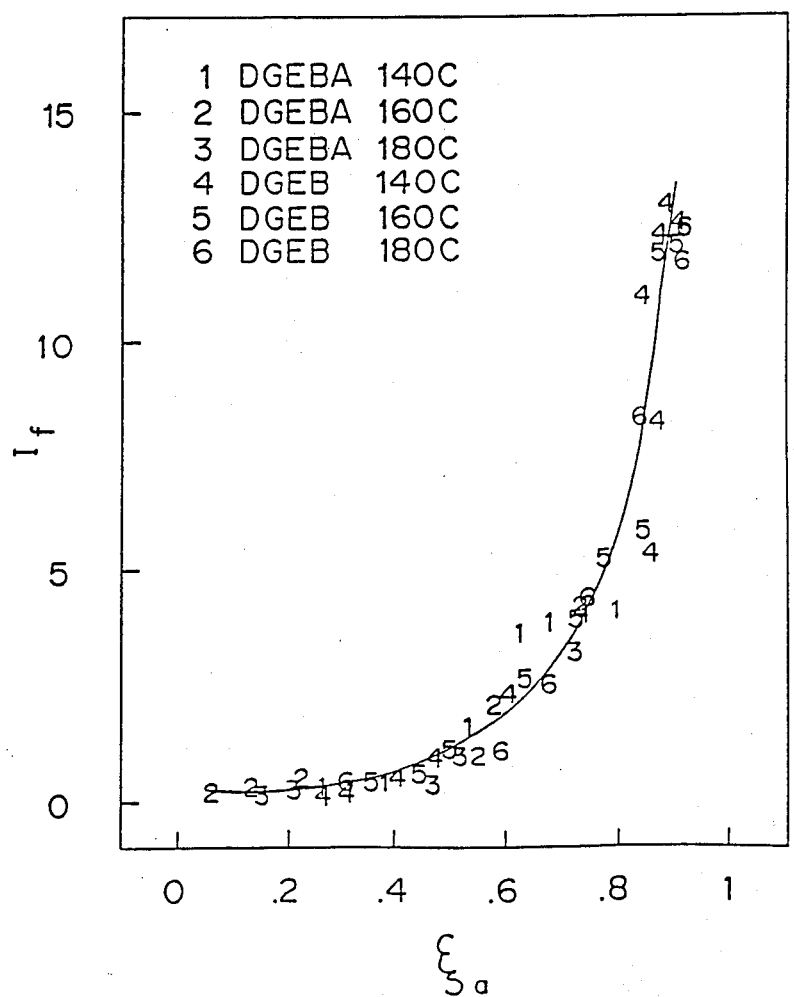
FIG. 8 is a graph of $I_f$ versus $\xi_a$ correlating relative fluorescence at 565 nm with the extent of amine reaction by UV-VIS.

In order to correlate fluorescence intensity at 565 nm with the overall extent of amine reaction, $I_F$ versus $\xi_a$ is plotted for both epoxies cured at three isothermal cure temperatures, 140° C., 160° C., and 180° C., shown in FIG. 8. In this figure, $\xi_a$ is estimated from deconvolution of UV-visible spectra. All the data fall on a single smooth curve whose slope is much sharper at later stages of cure, especially after gelation. In other words, this fluorescence is a very sensitive monitoring technique for cure beyond gelation, because its intensity comes mostly from tertiary amine products.

5. Molecular Weight and Soluble Fractions as a Function of Cure

By extending a recursive approach developed for ideal networks, Miller and Macosko in *Macromolecules* 13, 1063 (1980) derived molecular average properties of polymer networks in systems with first-shell substitution effects. This applies in the epoxydiamine system wherein the primary amine may have a different reactivity as compared with the secondary amine.

According to their theory, the weight average molecular weight, $M_w$ can be written for a stoichiometric mixture of epoxy-diamine as follows:

$$M_w = \{(\tfrac{1}{4})[1 + \xi_a(4\xi_a - \mu + 1)]M_A^2 + [1 + \xi_a(\mu - 1)]M_B^2 + 4\xi_a M_A M_B\} / \{[(\tfrac{1}{2})M_A + M_B][1 - \xi_a(\mu - 1)]\} \quad (23)$$

where $_a$ is the overall extent of cure reaction as defined by Eqn. (1), $M_A$ and $M_B$ are the molecular weight of the diamine and the diepoxide, respectively and is the weight average extent of reaction as defined by:

$$\mu = \frac{\Sigma i^2 A_i}{\Sigma i A_i} = \frac{A_{ps} + 4(A_{ss} + A_{pt}) + 9A_{st} + a6A_{tt}}{A_{ps} + 2(A_{ss} + A_{pt}) + 3A_{st} + 4A_{tt}}$$

$$= \frac{A_{ps} + 4(A_{ss} + A_{pt}) + 9A_{st} + 16A_{tt}}{4\xi_a} \quad (24)$$

Using $M_A = 212$ (DAA) and $M_B = 202$ (DGEB) or 340 (DGEBA), the molecular weight and soluble fractions as a function of cure can be determined. According to Eq. (8–12), expected values of $A_{ps}$, $A_{ss}$, $A_{pt}$, $A_{st}$ and $A_{tt}$ can be generated as a function $A_{pp}$ if r is known. For a given r value (for example, 1 or 1.5), a $\xi_a$, according to Eq. 1, and a corresponding $\mu$ value, according to Eqn. 25, is obtained from each set of expected values of cure products.

These values ($\xi_a$ and $\mu$) are substituted in Eqn. 23 to generate theoretical predictions of $M_w$ as a function of $\xi_a$. $M_w$ does not change much whether it is 1 or 1.5, as shown by the closeness of two solid lines.

One can determine concentration of each of the cure products by comparing these theoretical predictions with the experimental data from the UV-VIS curve deconvolution assuming at the early stages of cure, before gelation, only one side of diepoxide is reacted with diamine, leaving the other side unreacted in all cure products. This is a reasonable assumption when there are many unreacted diamines present, thus making molecular weight calculation of the cure species easy. In order to experimentally determine the molecular weight of the whole system, one needs to known the molecular weight of each cure species. With the molecular weight values of cure species (e.g., $A_{st} = M_A + 3M_B$) and compositional analyses (Table III), $\overline{M}_w$ of the epoxy system as a function of $\xi_a$ is easily estimated. The experimental values closely follow the theoretical prediction in the early stages of cure for both DGEBA and DGEB epoxy. However, as the cure approaches gelation, experimental points are much smaller than predicted, since the assumption is not valid at higher conversion.

Up to the gel point, all molecules are finite and therefore soluble. After the gel point, the weight soluble fraction, $W_s$, drops sharply. At 100% reaction, one expects to have an infinite network with no soluble species. Theoretical curves are derived as described in Miller & Macosko's paper in *Macromolecules*, 9, 206 (1976) and extended by Charlesworth in *J. Polym. Sci. Polym. Phys.*, 17, 1557 (1979). Part of the derivation as it applies to the present system is shown below:

$$W_s = W_{Af} P(F_A^{out})^4 + W_B P(F_B^{out})^2 \quad (25)$$

where $W_{Af}$ = wt. fraction of amine molecules,
$W_B$ = wt. fraction of epoxy molecules,
$P(F_A^{out})$ = probability that, looking out from an amine molecule, leads to a finite or dangling chain,
$P(F_B^{out})$ = probability that, looking out from an epoxy molecule, leads to a finite or dangling chain.

$P(F_A^{out})$ and $P(F_B^{out})$ can be expressed in terms of the extent of reaction, $\xi_a$, for $f=4$:

$$P(F_A^{out}) = \left(\frac{1}{\xi_a} - \frac{3}{4}\right)^{1/2} - \frac{1}{2} \quad (26)$$

$P(F_B^{out})$ is then defined as $$P(F_B^{out}) = \frac{P(F_A^{out}) - 1 + \xi_a}{\xi_a} \quad (27)$$

substituting Eqn. (26) and (27), $$W_s = W_{Af}\left[\left(\frac{1}{\xi_a} - \frac{3}{4}\right)^{\frac{1}{2}} - \frac{1}{2}\right]^4 + \quad (28)$$

-continued $$\frac{W_B}{\xi_{a2}}\left[\left(\frac{1}{\xi_a} - \frac{3}{4}\right)^{\frac{1}{2}} - \frac{3}{2} + \xi_a\right]^2$$

Figure 9:
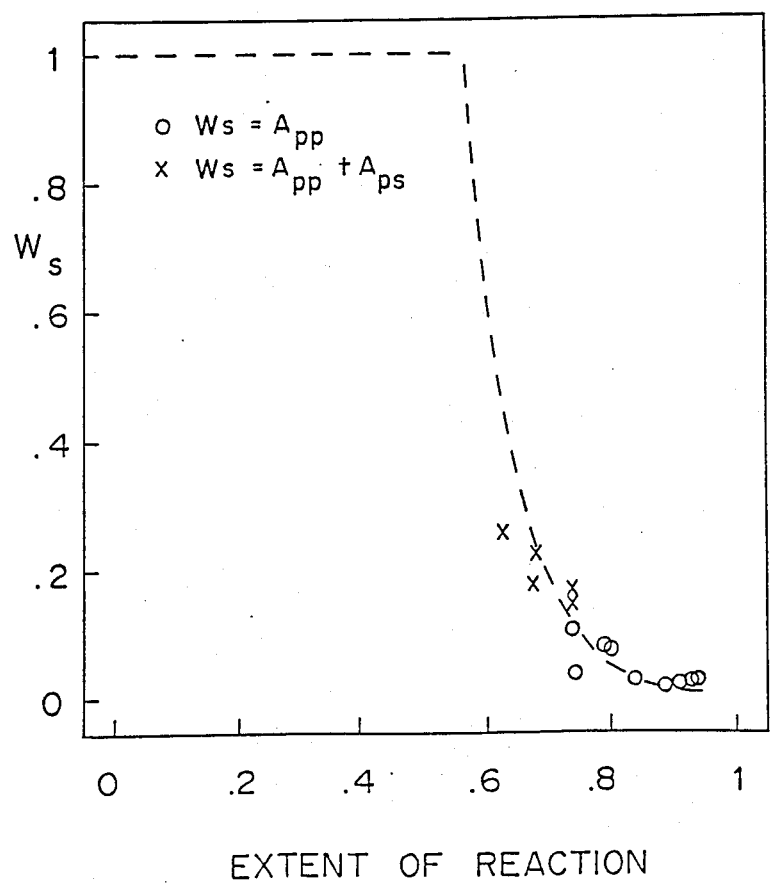
FIG. 9 is a comparison of the predicted weight soluble fraction as a function of the extent of amine reaction with composition of cure products.

The dotted line in FIG. 9 shows the predicted weight fraction soluble, $W_s$ as a function of $\xi_a$, according to Eqn. (28). Some cure product compositions are also indicated in FIG. 9. At high cure conversion ($\xi_a$ 0.8 for example), $W_s$ is only comparable to the unreacted DAA concentration ($A_{pp}$). This is quite reasonable since other cure products are expected to be incorporated into the network. At somewhat lower conversion ($\xi_a$ approximately 0.7), the soluble fraction seems close to the added fractions of unreacted DAA ($A_{pp}$) and $A_{ps}$, the first product of the cure. This result illustrates estimating the soluble fraction from cure product composition rather than from tedious and destructive solvent extraction studies.

6. IR Studies and Comparison with UV-VIS Studies

IR spectroscopy can be used to monitor the cure from the epoxide functionality simultaneously with UV-VIS and fluroescence studies following the cure reactions from the amine functionality of DAA. The extent of the epoxy reaction, $\xi_b$ for DGEBA-DDS epoxy, as defined by the following equation, $$\xi_b = 1 - \frac{A_{915\, cm^{-1}}(t)}{A_{1184\, cm^{-1}}(t)} \times \frac{A_{1185\, cm^{-1}}(o)}{A_{915\, cm^{-1}}(o)} \quad (29)$$

where $A_{915}$ cm$^{-1}$ is the IR absorption due to epoxy ring and $A_{1184}$ cm$^{-1}$ is the absorption due to C-C stretching of the bridge carbon atom in DGEBA can be plotted. For DGEB-DDS, $A_{1610}$ cm$^{-1}$ is used to calibrate for thickness fluctuation during cure, due to the phenyl ring in DDS, instead of $A_{1184}$ cm$^{-1}$. The curves are s-shaped, showing strong cure temperature effects, especially in the early stages of cure. The extent of epoxy cure, $\xi_b$ reaches about 80% maximum in DGEBA-DDS epoxy, and about 95% at 180° C. cure in DGEB-DDS epoxy. In DGEBA-DDS epoxy, a leveling-off at high conversion due to vitrification is observed. When compared at the same temperature, 160° C., greater cure is observed in DGEB-DDS than in DGEBA-DDS which is consistent with UV-VIS and fluorescence results.

In order to compare the extent of amine reactions of DAA and epoxide reactions, $\xi_a$ by UV-VIS deconvolution versus $\xi_b$ for three cure temperatures for DGEB-DDS epoxy, where the reaction is almost complete, is plotted. The straight line shows the slope of one which corresponds to the $\xi_a = \xi_b$ case. The data in general indicate that $\xi_a$ is somewhat greater than $\xi_b$ meaning faster consumption of DAA amine than overall epoxide. Since most of the epoxide reacts with DDS, this type of behavior is an indication that DAA may react a little faster than DDS. In order to confirm such differences in the reactivity between DDS and DAA, a scanning differential thermogram of a stoichiometric mixture of DEGB-DDS is compared with that of DGEB-DAA. Even though the areas under the exotherm are not very different, DGEB-AA epoxy has an exotherm at a lower temperature, about 20° lower, indicating a faster cure reaction by DAA than DDS. Therefore, a calibration curve should be used in order to correlate the extent of reaction monitored by DAA with the extent of overall reaction in DDS containing epoxy.

EXAMPLE OF MEASURING THE EXTENT OF CURE BY DGEB-MDA LABELLED WITH DAS p,p'-diamino stilbene (DAS) is used as a reactive label in another important epoxy amine resin, DGEB-MDS. DAS is selected since it is expected to have a reactivity similar to the curing agent, methylene dianiline (MDA), according to the Hammet constant reported by O. Exner in "A Critical Compilation of Substituent Constants" in *Correlation Analysis in Chemistry* by N. B. Chapman and J. Shorter, p. 457 (Plenum Press, NY 1978). Unlike DAA, DAS is highly fluorescent even when the amine groups are primary, providing a greater sensitivity at early stages of cure. The photophysical behavior of trans stilbene and some of its derivatives are known to be sensitive to environmental viscosity. Thus, one can expect to see the effects on photophysical behavior from both the increasing viscosity and the chemical reaction as cure proceeds. DGEB was chosen since the cure reaction can progress much further at cure temperatures above 80° C. due to the absence of vitrification.

DGEB (98% purity) was purchased from Aldrich and used without further purification. MDA was recrystallized from toluene. DAS-dihydrochloride from Aldrich was neutralized with sodium carbonate and recrystallized from methanol to obtain the free amine.

A stoichiometric mixture of DGEB and MDA was used with 0.1% of DAS as a label. Sample preparation method was the same as in the previous example. A Perkin-Elmer UV-VIS Diode Array (Model 3840) and Fluorescence Spectrometer (MFF-66) with a Model 7500 Data Station were used to record the spectra. UV-VIS and fluorescence spectra were obtained after cooling the sample to room temperature following cure in an oven for a specific time. Fully substituted DAS (tt-DAS) was synthesized by reacting DAS with a large excess of phenyl glycidyl ether (PGE) at 140° C. for 12 hours, followed by removal of the excess PGE under vacuum. A UV-VIS absorption peak at 372 nm was observed for tt-Das. The extent of reaction based on epoxy ring disappearance was estimated by monitoring IR absorption at 915 cm$-1$ (epoxy ring) corrected with the absorption at 1610 cm$-1$ (MDA internal standard).

1. Uv-visible absorption spectra

Figure 10A:
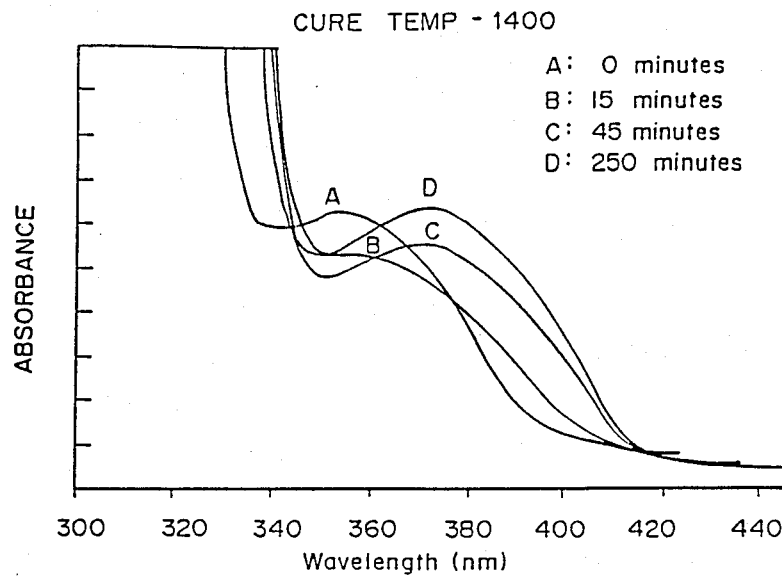
FIG. 10 is the UV-VIS absorption spectra (FIG. 10a) and fluorescence spectra (FIG. 10b) of DAS in DGEB-MDA epoxy as a function of cure time at 140° C.

FIG. 10h shows the UV-VIS spectra of DGEB-MDA-DAS (0.1%) following cure at 140° C. Before cure, DAS absorption maxima is at 352 nm. DAS in DGEB shows another absorption peak at 327 nm, which is hidden under MDA absorption in DGEB-MDA epoxy. As cure proceeds, red shifts of the peak at 352 nm occur. After 300 minutes of cure at 140° C., the DAS absorption peak is shifted to 371 nm. Further curing, even at high temperatures, does not increase this absorption beyond 372 nm.

Red shifts in DAA and DAS are caused by the electron donating effect of the tertiary amines as compared to the primary amines. Assuming that such electronic effects are of similar magnitude for DAA and DAS, one would expect smaller red shifts in DAS compared to DAA. This is due to the fact that it requires greater energy to produce the same shifts in the uv region where DAS absorbs as compared to the visible region where DAA absorbs. Due to such small shifts in DAS labelled epoxy, it is not possible to deconvolute the absorption spectra.

2. Fluorescence Spectra

Figure 10B:
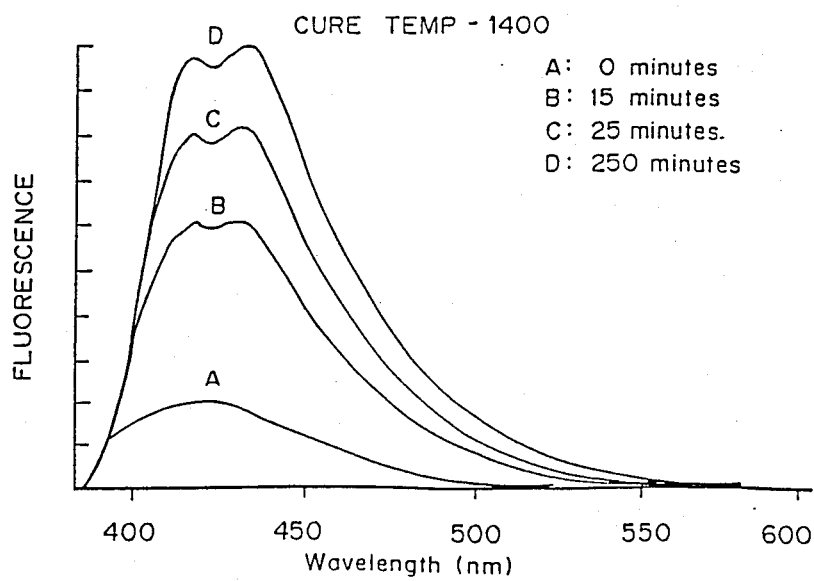

FIG. 10b shows fluorescence spectra as a function of cure time at 140° C. At zero cure time, the emission maximum is at 418 nm and a shoulder at 403 nm. As cure time increases, enhancement of emission as well as splitting into two peaks (at 418 nm and 430 nm) occur, as shown in FIG. 10b. The emission spectra of tt-DAS in dilute solution of PGE shows the same two peaks, apparently red shifted as in UV-VIS spectra. The ratio of fluorescence quantum yield of tt-DAS to DAS in dilute solution is found to be about 2.4 at 418 nm.

Figure 11:
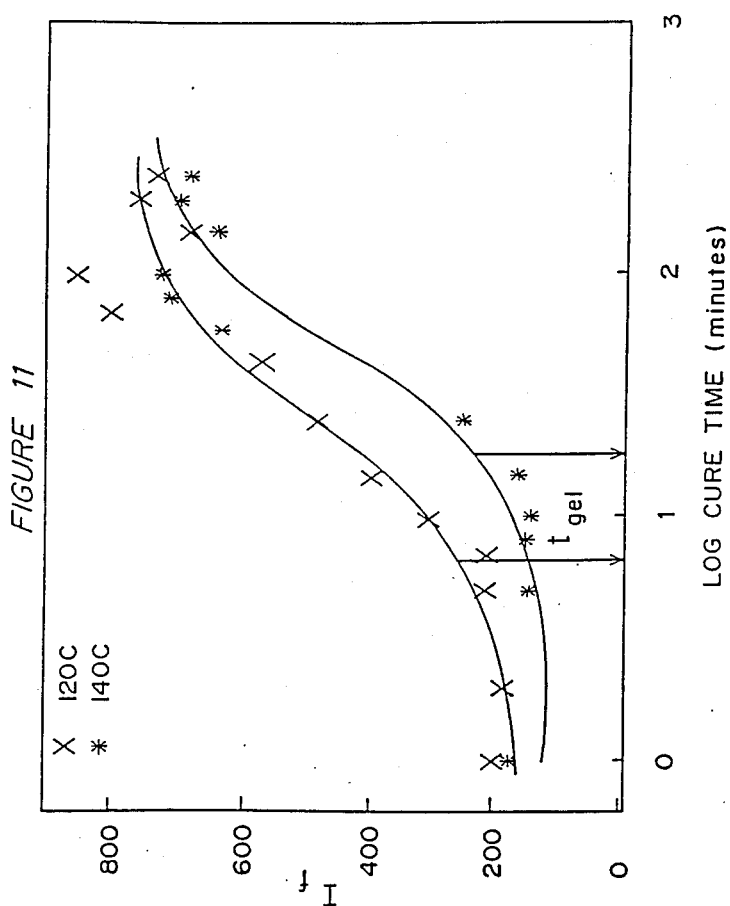
FIG. 11 is the fluorescence intensity at 418 nm as a function of cure time at 140° C. and 120° C. in DAS labelled DGEB-MDA epoxy.

FIG. 11 shows the s-shaped curves of the emission intensity at 418 nm as a function of cure time at two cure temperatures, 140° and 120° C., respectively. At these temperatures, the gel time for DGEBA-MDA epoxy is known to be about 8 min. and 16 min, respectively. One may assume that the gel times are similar for DGEB-MDA epoxy. After gelation, fluorescence emission increases sharply at the respectively cure temperature. Also, it is noted that the overall increase in emission intensity is usually about 3 to 3.5 times greater as compared to zero cure time at longer cure times.

Emission intensity of tt-DAS in DGEB-MDA epoxy is relatively constant until the later stages of cure. From this behavior, one can conclude that the chemical reaction, substitution on DAS amine groups, is the main cause for the emission enhancement near gelation but that viscosity effect begins to contribute to the enhancement of the emission at later stages of cure.

A plot of fluorescence intensity at 418 nm as a function of cure based on the epoxy ring disappearance shows that the fluorescence intensity increases sharply after gelation, thus allowing for sensitive cure monitoring during the later stages of cure.

EXAMPLE OF CHARACTERIZING THE POLYMERIZATION OF POLYURETHANES LABELLED WITH NDI

1. Synthesis of Model Compounds for Determination of the Quantitative Composition Over a Wide Range of Cure Extent 1,5-naphthalene diisocyanate (NDI) (Columbia Chemicals) in toluene less than 0.01N was reacted with excess n-butanol (approx. 0.4N) at 50°, 60° and 70° C. Before adding n-butanol, the NDI solution was filtrated to assure real solution. A Perkin-Elmer Lambda Diode Array UV-VIS spectrophotometer and a Perkin-Elmer MPF-66 fluorescence spectrophotometer were, respectively, used for absorbance and emission measurement. 60 ul of reacted solution at each time was injected into 3 ml quartz cell, (O.D. approx. 0.6), for UV absorbance measurement; 10 ul solution, (O.D. approx. 0.1), for fluorescence measurement. The emission spectra were collected by exciting the samples at 314 nm.

Urethano-isocyanate and urethane were obtained from analytical normal phase HPLC using a Varian system. The normal phase column was employed, using a solvent programmer gradient and varying amounts of tetrahydrofuran in hexane. A UV detector was set at 314 nm.

2. Reaction Kinetics

The reaction mechanism is as follows

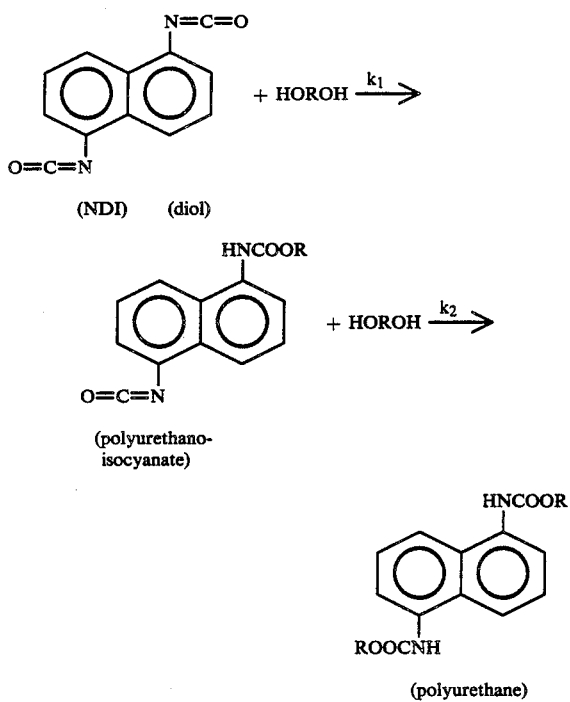

(NDI) (diol)

(polyurethano-isocyanate)

(polyurethane)

This mechanism yields the following kinetic equations:

$$d[NDI]/dt = -k_1[NDI][OH]^n$$

$$d[UI] = k_1[NDI][OH]^n - k_2[UI][OH]^n$$

$$d[U]/dt = k_2[UI][OH]^n$$

For convenience of analysis, the reaction can be simplified as two simple consecutive pseudo first order reactions by adding an excess of n-butanol. Then, the eqns. can be solved as:

$$[NDI]/[NDI]_0 = e^{-k'_1 t} \quad (30)$$

$$[UI]/[NDI]_0 = [R/(1-R)][e^{-k'_1 t} - e^{-k'_1 t/R} - 1] \quad (31)$$

$$[U]/[NDI]_0 = [R/(1-R)][(1 - e^{-k'_1 t})/R + (-e^{-k'_1 t/R} - 1)] \quad (32)$$

Where $k'_1 = k_1[OH]^n$, $k_2' = k_2[OH]^n$, $R = k_1'/k_2' = k_1/k_2$, $[OH] = [OH]_0$, and $[NDI]_0$ and $[OH]_0$ represent the initial concentrations of the diisocyanate and the n-butanol.

The quenching effects of isocyanate and n-butanol on urethanes have been examined and found to be negligible. The absorbance of solutions for fluorescence measurement were adjusted to be smaller than 0.12 to assure the linear relationship between concentration and the fluorescence intensity. Thus, the fluorescence intensity can be expressed in terms of fractions of the NDI, urethano-isocyanate (UI) and urethane (DU).

$$I_{\beta 57 nm} = F_{NDI}[NDI] + F_{UI}[UI] + F_{DU}[DU] \quad (33)$$

Compared to the other two species, NDI fluorescence is negligible. Thus, $F_{NDI}$ can be overlooked. By HPLC, the urethano-isocyanate and urethane were separated to quantify $F_{UI}$ and $F_{DU}$. The fluorescence dependence is simplified as $I_f(k_1', R, t)$. $I_f(k_1', R, t)$ were analyzed by using nonlinear regression for $k_1'$ and R values.

The fractions of NDI, urethano-isocyanate and urethane were obtained by deconvoluting the UV absorption spectra. The pure NDI, urethano-isocyanate and urethane obtained from analytical HPLC were characterized to obtain standard spectra.

3. Results

Figure 12:
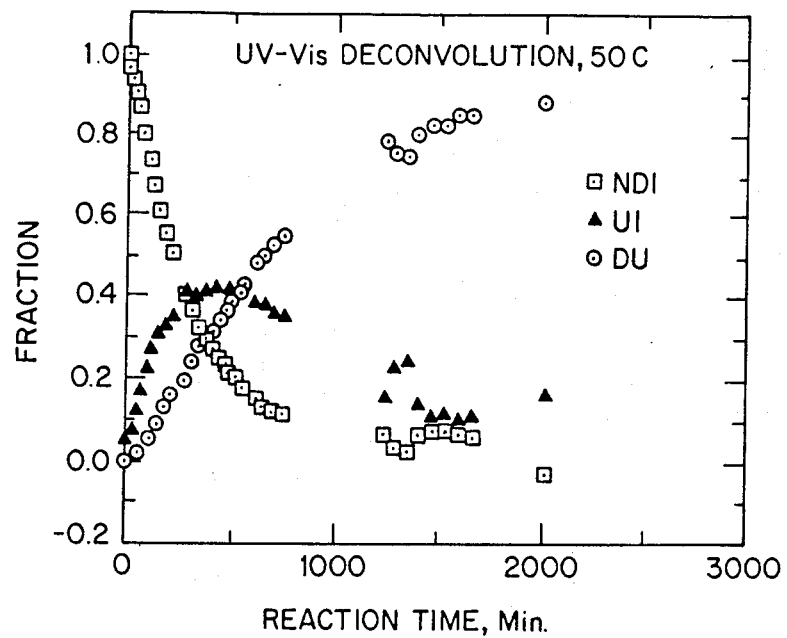
FIG. 12 is a plot of relative product and reactant concentrations versus time for a representative urethane polymerization at 50° C.

FIG. 12 shows the change in composition as a representative reaction proceeds. As can be seen in FIG. 12, at time zero, the reaction mixture contain no diurethane (DU) or urethano-isocyanate (UI) but is rich in NDI. As the reaction proceeds, the NDI fraction drops sharply while the DU and UI fractions climb. The UI intermediate reaches a peak and then proceeds downward as the DU curve approaches a value of 100%.

We obtained $K'_1$ from the slope of the plot of $\ln[NDI]$ versus time. The value of $K'_1$ then is substituted into the above equations (31) and (32). For a series of R values, it is possible to generate a series of the curves of [UI] and [DU] as a function of reaction time. By comparing these curves with the experimental points, it is possible to find the best fitted R value. Table IV summarizes the results on $K'_1$, $K_1$, as well as R value obtained at 50°, 60° and 70° C. Since R is equal to $K_1/K_2$, the results mean that $K_2$ is always smaller than $K_1$, a tendency in agreement with previous studies by IR or titration techniques.

TABLE IV

| Rxn Temp | [OH] M | UV technique | | | Fluoroescence technique | | |
|---|---|---|---|---|---|---|---|
| | | $K_1' \times 10^2$ min$^{-1}$ | $K_1 \times 10^2$ M$^{-1}$min$^{-1}$ | R= $K_1/K_2$ | $K_1' \times 10^2$ min$^{-1}$ | $K_1 \times 10^2$ M$^{-1}$min$^{-1}$ | R= $K_1K_2$ |
| 50 C. | 0.155 | 0.21 | 1.35 | 2.86 | 0.18 | 1.16 | 2.94 |
| 60 C. | 0.433 | 1.20 | 2.77 | 2.50 | 1.10 | 2.54 | 2.67 |
| 70 C. | 0.433 | 1.60 | 3.69 | 2.22 | 1.45 | 3.35 | 2.50 |

| Activiation Energy (kcal) | UV technique | Fluor. technique | Average |
|---|---|---|---|
| $K_1$ | 11.1 | 11.7 | 11.4 |
| $K_2$ | 13.9 | 13.5 | 13.7 |

Figure 13:
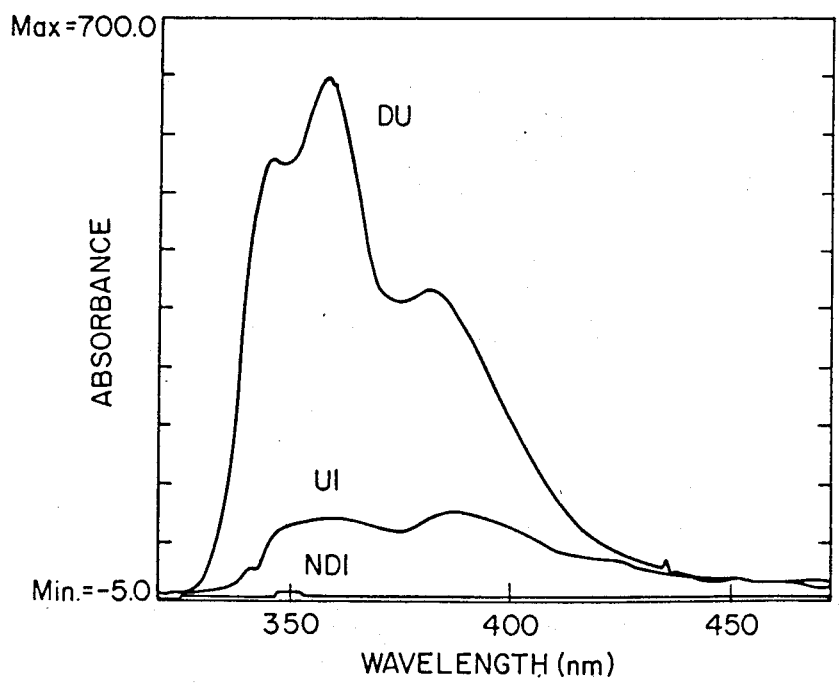
FIG. 13 is a plot of the normalized fluorescence spectra of NDI, urethano-isocyanate (UI) and urethane (DU) in toluene.

FIG. 13 shows the normalized fluorescence spectra of NDI, UI and DU in toluene. The relative fluorescence due to DU is much greater than that of UI or NDI. Thus, by determining the fluorescence intensity at 357 nm, it is possible to determine the sample composition and thus extent of reaction.

Figure 14:
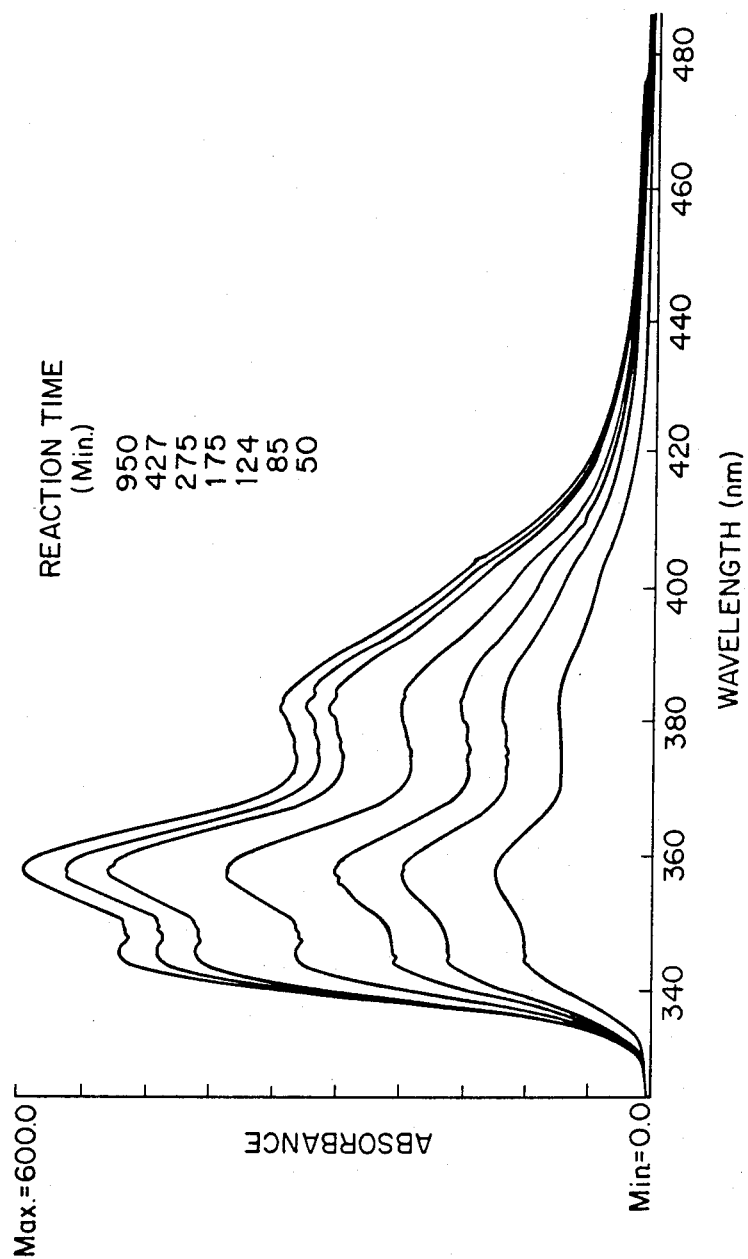
FIG. 14 is a plot of the fluorescence spectrum versus time for a representative urethane polymerization.

FIG. 14 shows the overall fluorescence spectrum of the reaction mixture as a function of reaction time. In FIG. 14, each fluorescence intensity plot represents the fluorescent spectrum of the reaction mixture at a particular time, with plots of greater fluorescent intensity corresponding to greater reaction times. Note that the peak fluorescent intensity is at approximately 357 nm.

Figure 15:
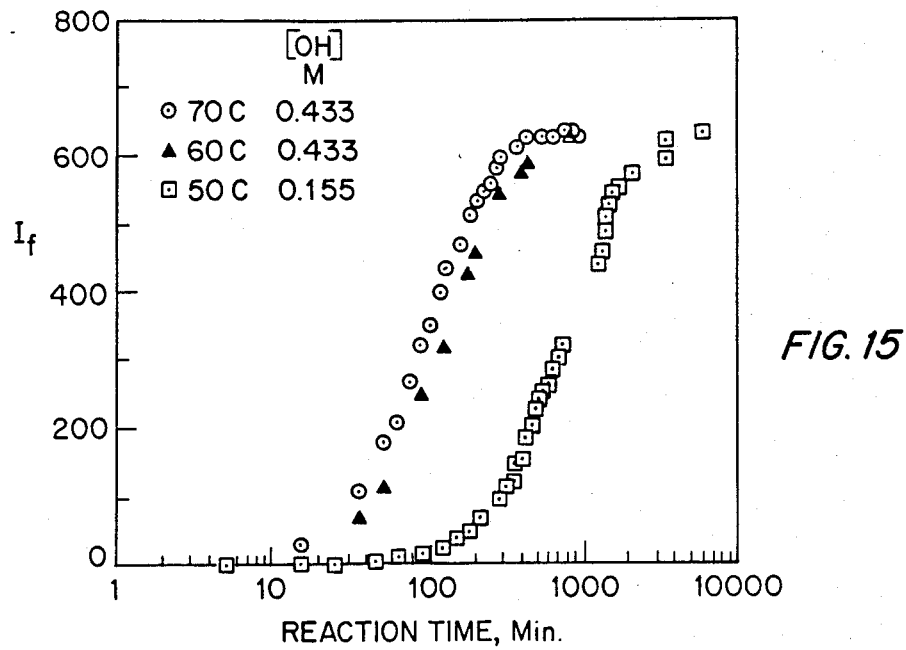
FIG. 15 plots fluorescence intensity versus reaction time for three representative urethane polymerization reactions.

FIG. 15 plots fluorescent intensity at 357 nm as a function of reaction time for three different sample runs.

Since the fluorescence of the NDI species is negligible even at high concentration, we can write Eqn. (33) to account for the overall intensity.

$$I_f = 150[UI] + 630[DU] \quad (34)$$

By substituting Eqn. (31) and (32) in Eqn. (34), we obtain Eqn. (35)

$$I_f = 150[R/(1-R)][e^{-K'_1 t} - e^{-K'_1 t/r}] \\ + 630[R/(1-R)][(1-e^{-K'_1 t})/R + \\ (-e^{-K'_1 t/R} - 1)] \quad (35)$$

From the experimental points of $I_f$ versus time as in FIG. 15, we find the best fitted values of R and $K_1'$ by nonlinear regression analysis by initially using the set of R and $K_1'$ values from UV-VIS deconvolution. The experimental data in FIG. 15 can be simulated by a set of the best fitted R and $K_1'$ values listed in Table IV. Table IV also provides the activation energies ($\Delta E^*$) for $K_1$ and $K_2$. The agreement between the UV-VIS technique and the fluorescence technique is quite good in all the kinetic parameters ($K_1'$, $K_1$, R and $\Delta E^*$). The activation energies are comparable to the values reported by the IR or titration methods. See, for example, Burkus, et al. *J. Am. Chem. Soc.*, 80, 5948 (1958); Barbalata, et al., *European Polymer J.*, 14, 427 (1978) and Ferstanding, et al., *J. Am. Chem. Soc.*, 81, 4838 (1959).

Figure 16:
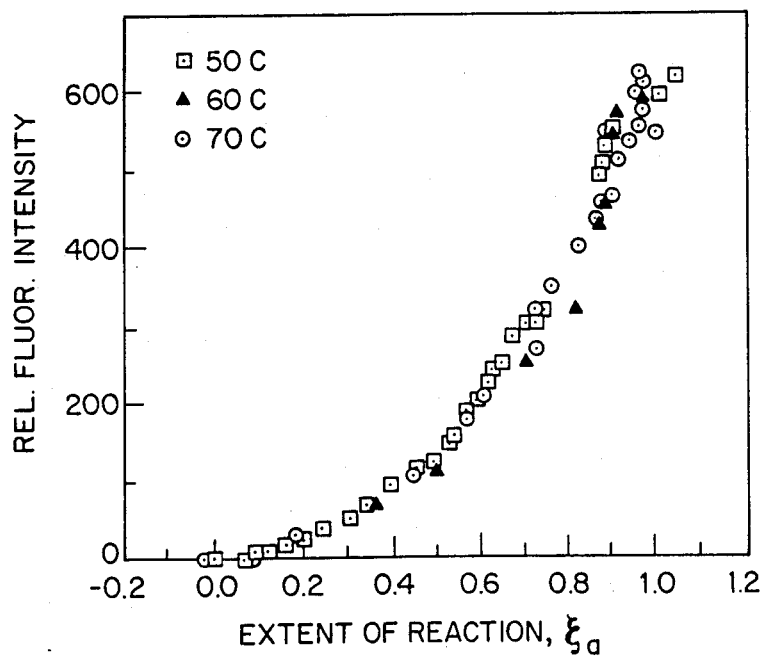
FIG. 16 plots the fluorescence intensity versus the overall extent of reaction in polyurethane synthesis.

Finally, a calibration curve to relate $I_f$ to the overall extend of reaction, $\xi_a$ is obtained as shown in FIG. 16.

Similarly, the process may be used to determine cure extent in compounds similar to urethane, such as urea, ($H_2NRNH_2$). In the urea curing process, the diamine reacts with NDI to form polyureanoisocyanate which is analogous to the polyurethanoisocyanate described previously. The polyureanoisocyanate then reacts with a second amine to form polyurea, (analogous to polyurethane). In a manner similar to that described for polyurethane, the intensity of fluorescence is measured to allow a determination of cure extent.

Finally, it is also possible to use this method to determine the extent of cure for polymer systems comprising polyimides and polyetherimides using diamines of highly conjugated aromatic compounds such as napthyl diamine and anthracenyl diamine.

A representative reaction using a diamine (DAN) such as naphthyl diamine to monitor the polymerization of a poly(amic acid) (PAA) is given below:

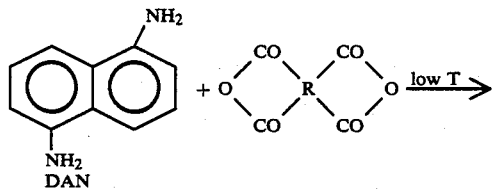

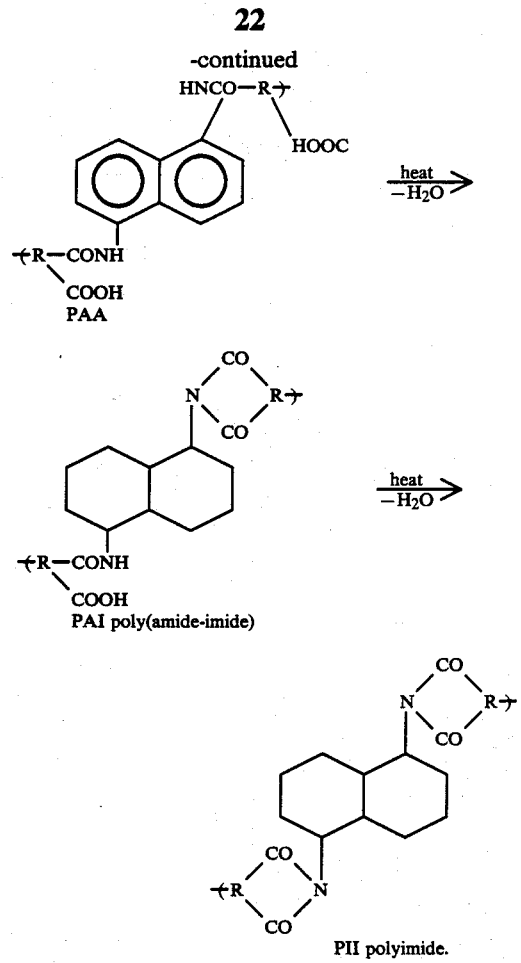

This three step process is charted by both UV-Visible Spectra and Fluorescent Spectra in FIGS. 17-22.

Figure 17:
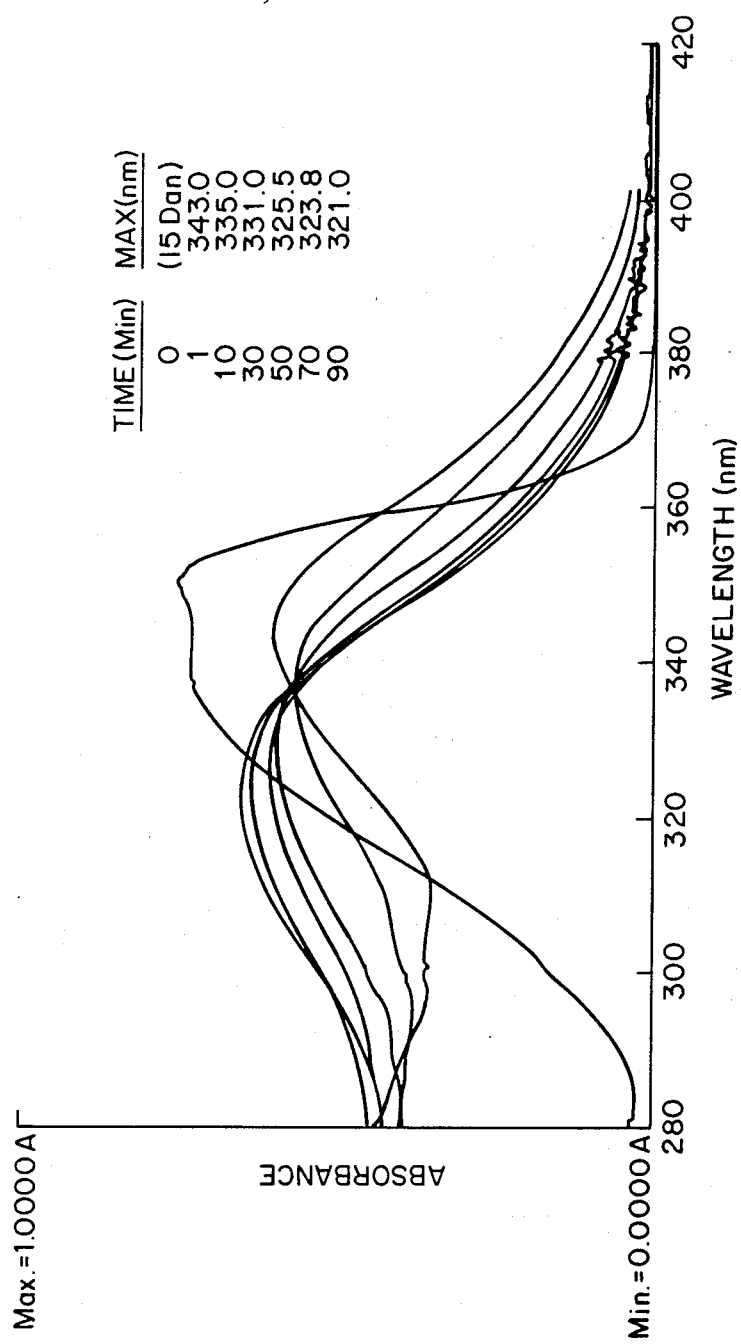
FIG. 17 plots the UV-Visible spectrum over the course of a poly(amic acid) synthesis reaction.

FIG. 17 plots the UV-Visible spectrum of naphthyl diamine (DAN) and poly(amic acid) (PAA) during PAA synthesis. At time zero an absorption at about 352 nm is observed for DAN. As the reaction progresses over a 90 minute period, the peak absorption experiences a blue shift. This shift is complete when the PAA synthesis is complete, having an absorption at about 321 nm.

Figure 18:
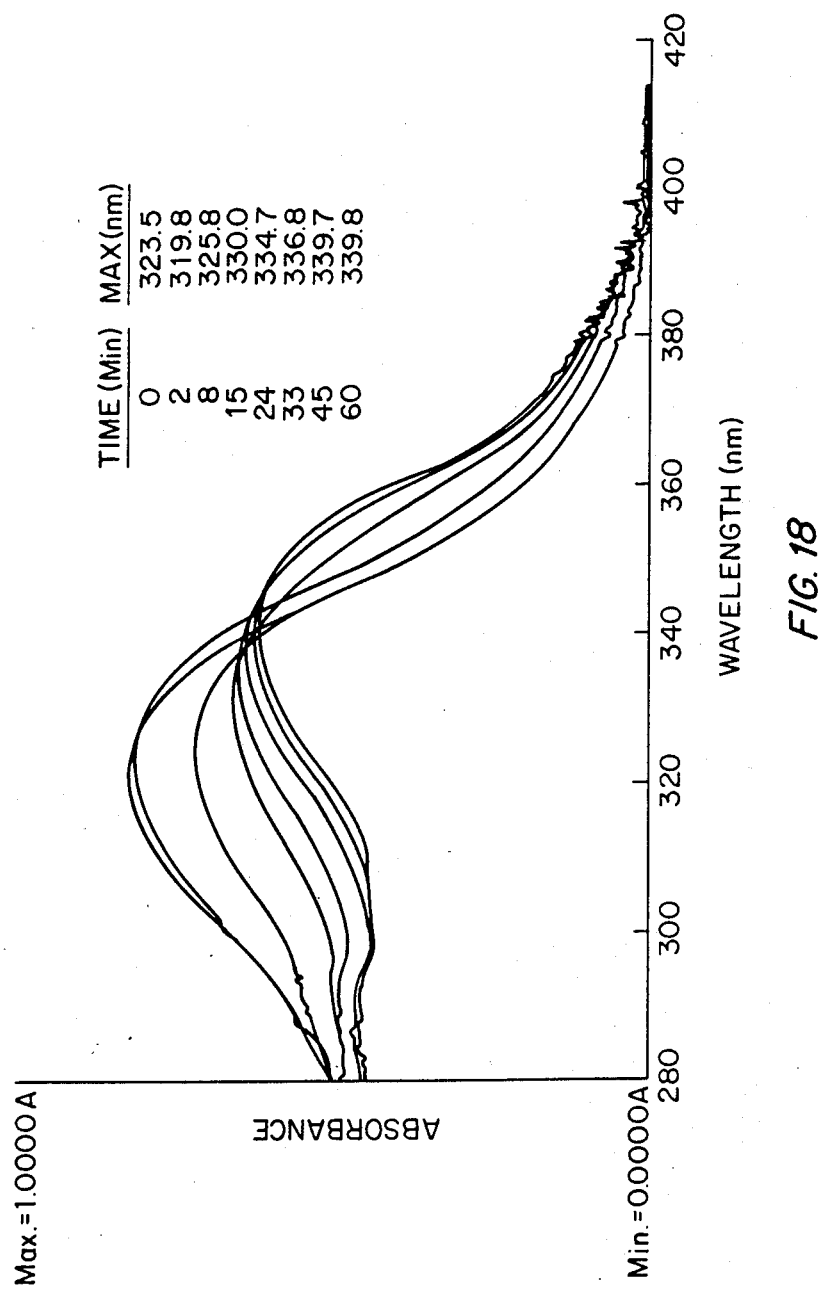
FIG. 18 plots the UV-Visible spectrum for the first 60 minutes of the reaction in which poly(amic acid) is converted to poly(amide-imide).

The next Figure, FIG. 18 shows a red shift which occurs as PAA undergoes a dehydration synthesis at about 150° C. to form PAI. Over a 60 minute time period, the absorption is seen to decrease and shift from about 323.5 nm to 339.8 nm.

Figure 19:
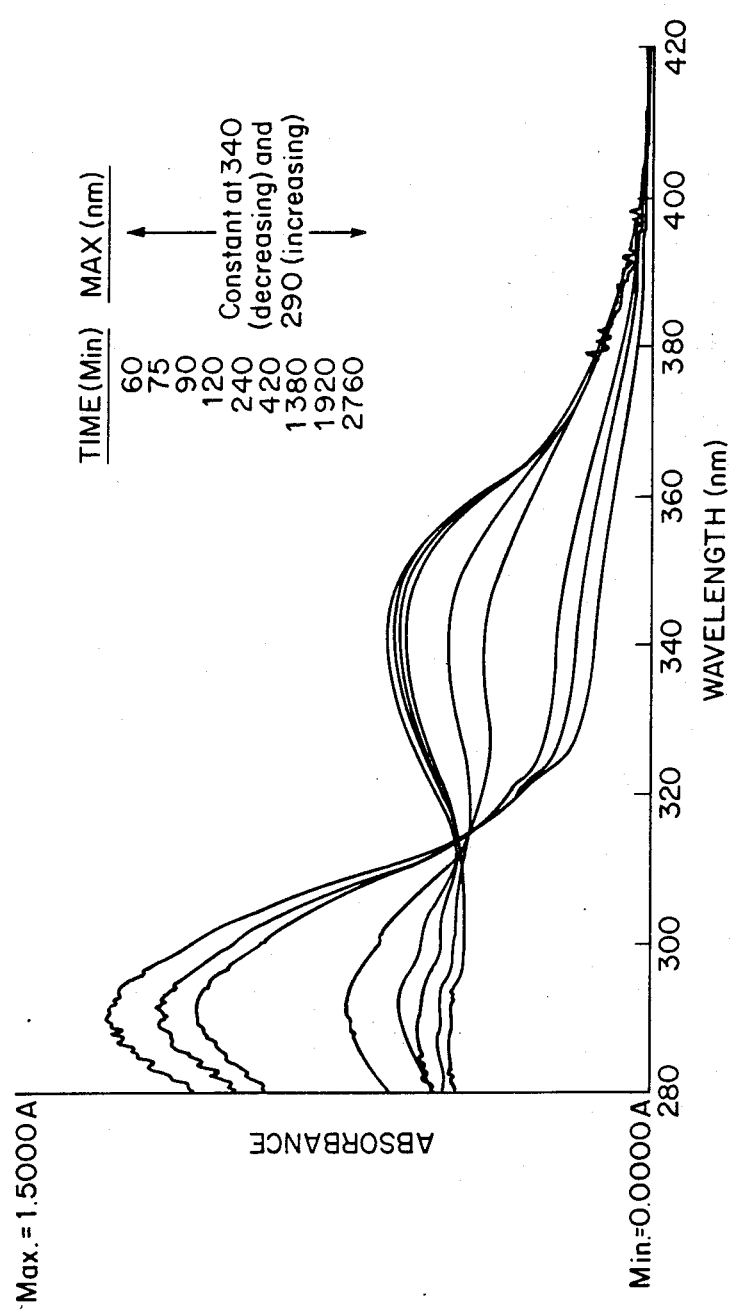
FIG. 19 plots the UV-Visible spectrum of the reaction in FIG. 18 over the time domain of 60-2760 minutes in which poly(amine-imide) undergoes reaction to form poly(imide).

FIG. 19 continues the data of FIG. 17 into the 60-2760 minute domain. In this domain, a second, larger blue shift occurs as the dehydration synthesis continues. However, this shift is due to PAI forming PII rather than due to PAI synthesis. As seen in FIG. 19, the absorption at about 340 nm decreases, indicating a reduction of PAI concentration. This reduction occurs with a simultaneous increase of absorbance at about 290 nm indicating PII synthesis.

Figure 20:
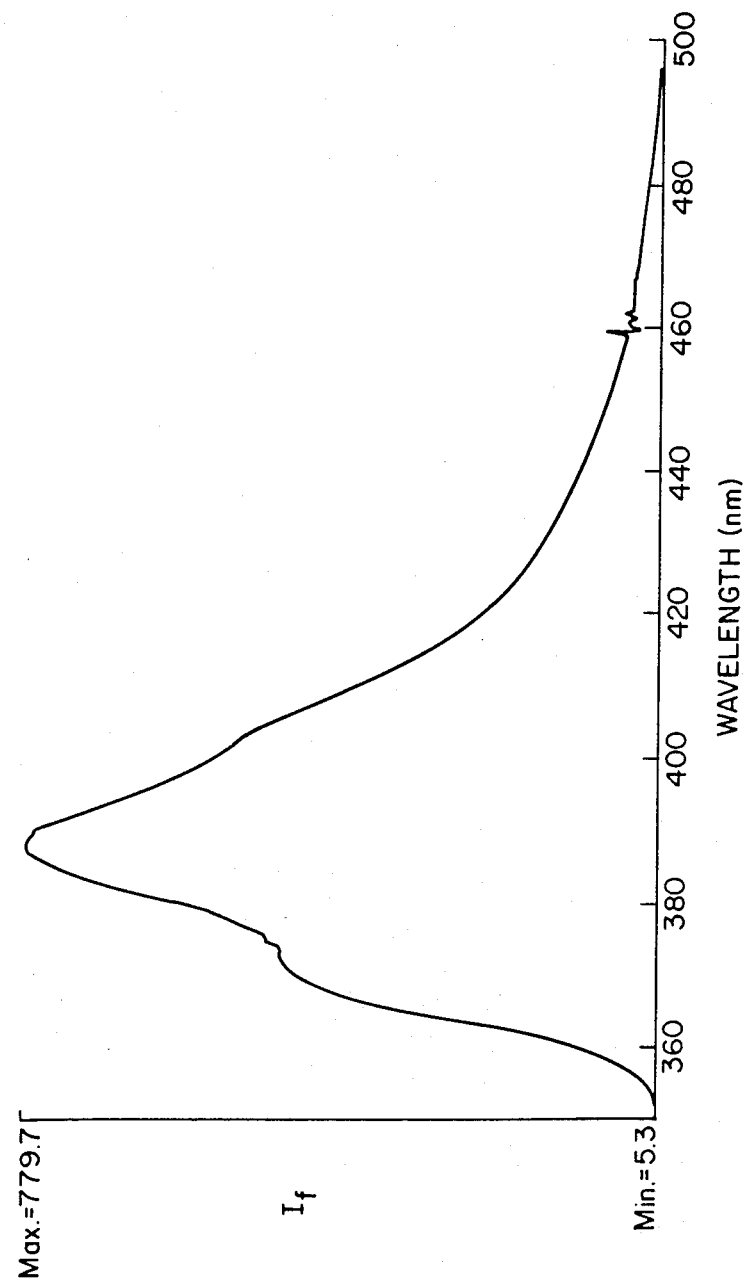
FIG. 20 is the fluorescence spectrum of DAN.

In FIG. 20, the fluorescent intensity spectrum of DAN prior to PAA formation is plotted. At a concentration equal to that used in determining the UV-Visible spectra, a strong peak intensity was observed at 388 nm.

Figure 21:
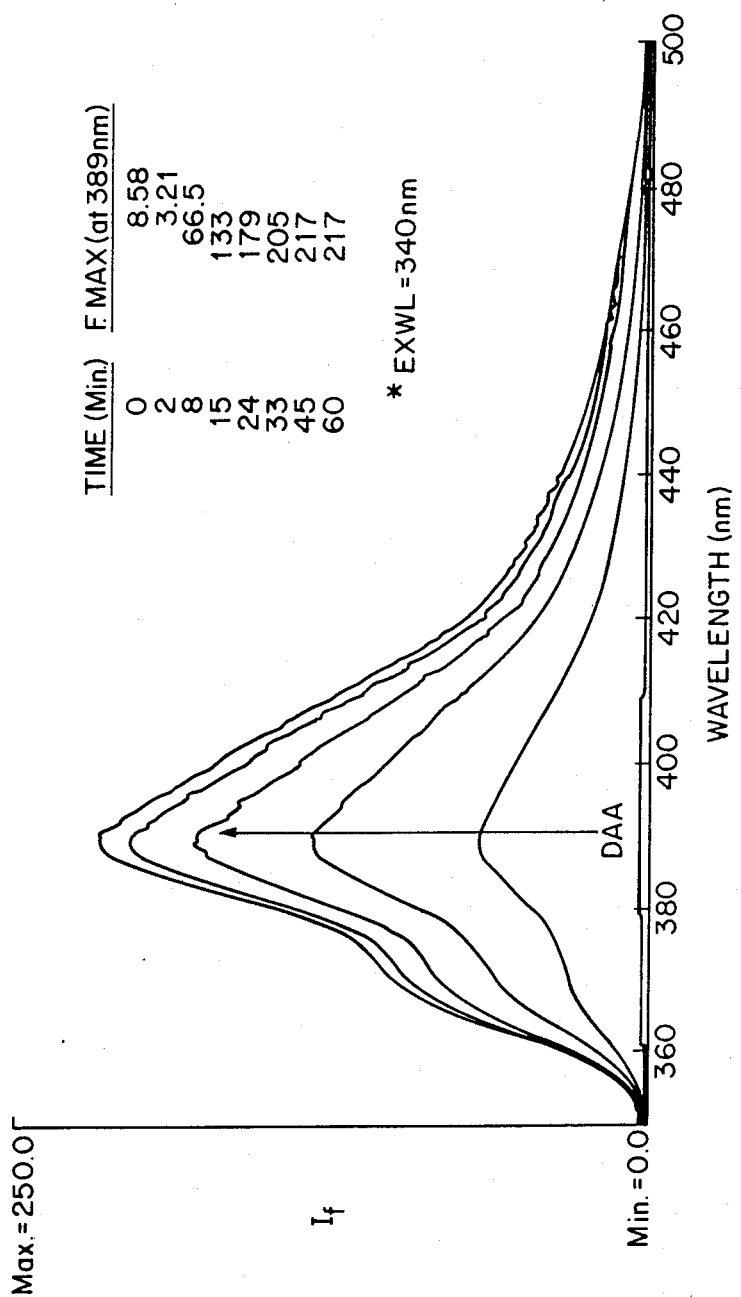
FIG. 21 is the fluorescence spectrum of a representative reaction of PAA to PAI over a 60 minute period.

FIG. 21 is a plot of the fluorescence intensity spectrum during the synthesis of PAI from PAA. Over the 60 minute duration, the intensity of fluorescence at about 389 nm was seen to increase from near zero (pure PAA) to a value of about 25% of the observed with DAN. This increase is a result of the increased PAI concentration in the reaction mixture.

Figure 22:
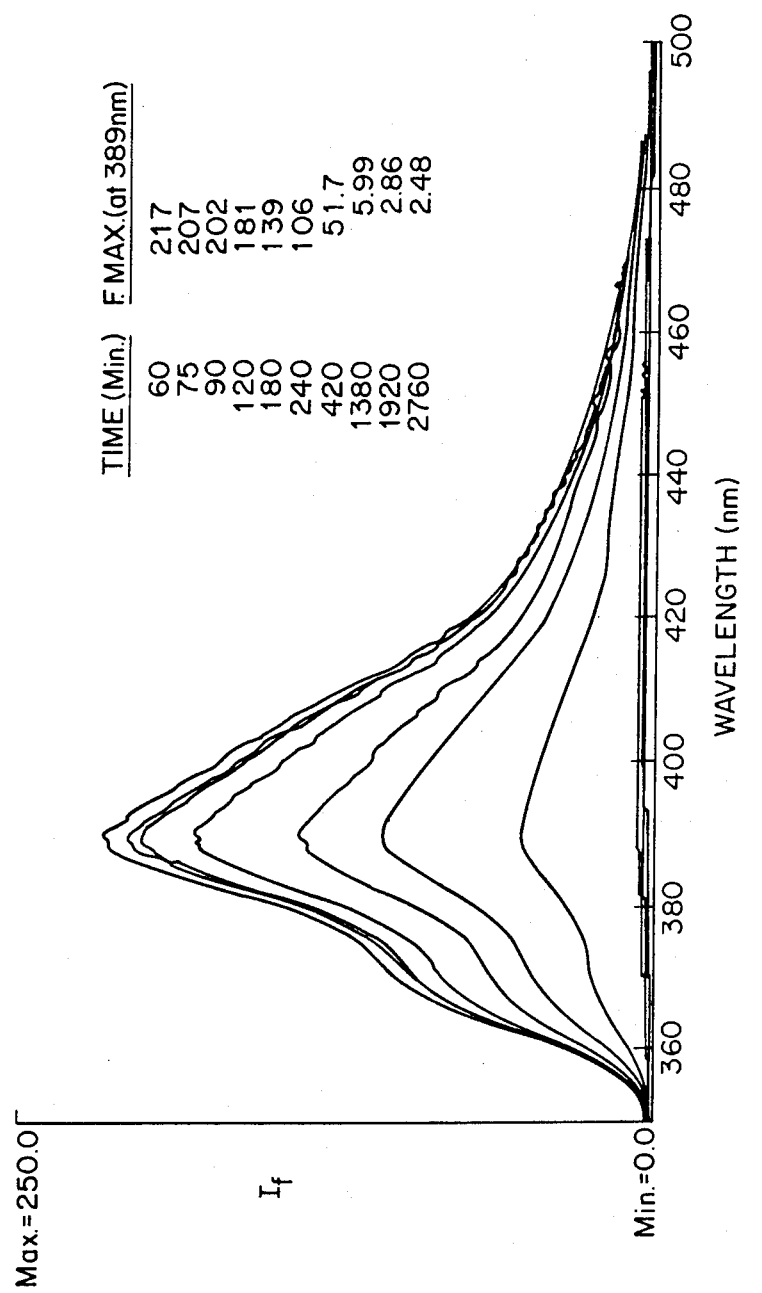
FIG. 22 is the fluorescence spectrum of a representative PAI to PII reaction over the time of 60-2760 minutes.

Finally, as shown in FIG. 22, in the time domain of 60 to 2760 minutes, the fluorescent intensity at about 389 nm drops by almost 99% as the reaction continues, converting PAI to PII.

Figure 23:
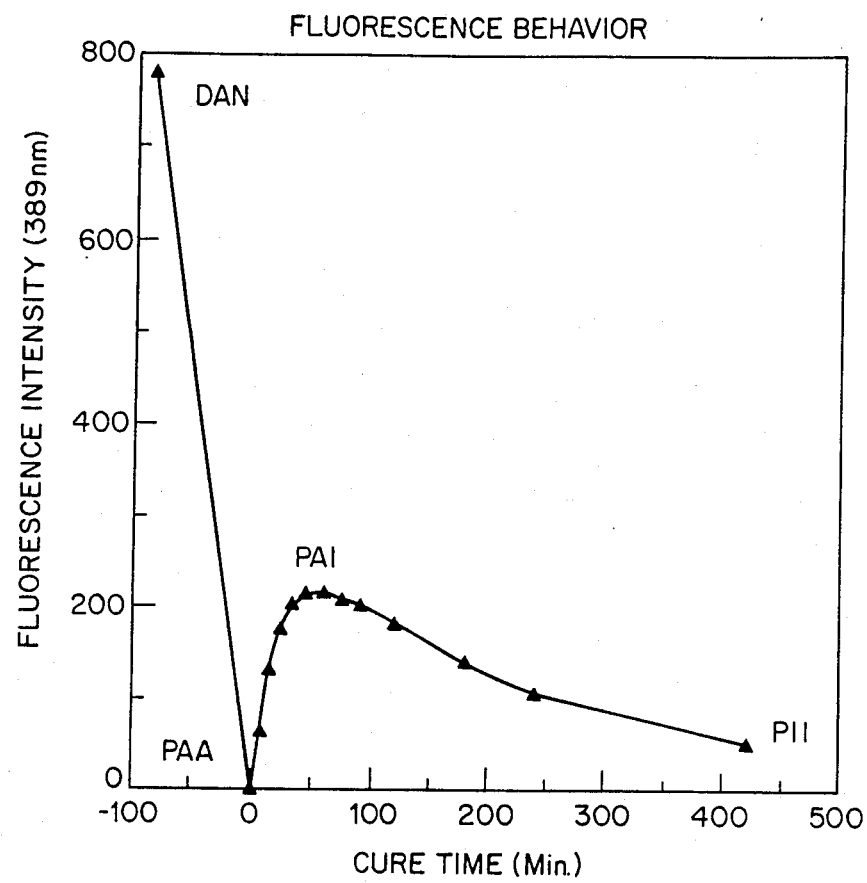
FIG. 23 is a plot of fluorescence intensity at 389 nm for the reaction DAN to PAA to PAI to PII.

The fluorescent intensity at the 389 nm peak is plotted against cure time in FIG. 23. As the figures shows, the fluorescence of DAN is virtually nonexistent in the PAA produced using the DAN reactant. As the PAA is heated and undergoes a PAI synthesis, the fluorescence intensity at 389 nm rises sharply to a value of approximately one quarter of that observed with DAN. As the PAI reacts to form PII, the fluorescence gradually decreases to zero. Thus, by comparing measured fluorescence intensity values to a curve such as is given in FIG. 22, it is possible to determine the extent of cure in the polymer system for the production of polyimides. Furthermore, as in the urethane/urea analogy, it is possible to analyze the polyetherimides to the polyimides and achieve the same result.

EQUIVALENTS

The present invention may be embodied in other specific forms without departing from the spirit and scope thereof. These and other modifications of the invention will occur to those skilled in the art and are intended to fall within the scope of the appended claims.

I claim:

1. A polymer system for producing a polymer cure product selected from the group consisting of polyimides, polyetherimides, polyurethanes and polyureas, said system comprising at least one precursor, a curing agent and a label, wherein the label reacts with the precursor at a rate comparable to the reaction rate of the curing agent with the precursor, said label and the concentration of said label selected to produce a fluorescence intensity proportional to the concentration of polymer cure products.

2. A polymer system of claim 1, wherein the precursors are selected from the group consisting of: polyols, dianhydrides, diisocyanates and diamines, and the curing agent is a diisocyanate or a diamine.

3. A polymer system of claim 2, wherein the precursor comprises a diisocyanate having ether linkages.

4. A polymer system of claim 1, wherein the label is selected from the group consisting of aromatic diisocyanates and diamines of conjugated aromatic compounds.

5. A polymer system of claim 4, wherein the label is selected from the group consisting of: naphthylene diamine, anthracenyl diamine and naphthylene diisocyanate.

6. A method for determining the extent of polymerization of a polymer system for producing a polymer cure product selected from the group consisting of polyimides, polyetherimides, polyurethanes and polyureas, said system including at least one precursor and a curing agent, comprising the steps of:
   a. adding a label to the polymer system, said label reacting with the precursor at a rate comparable to the reaction rate of the curing agent with the precursor, said label being selected and added at a concentration producing a fluorescence intensity proportional to the concentration of polymer cure products;
   b. polymerizing the polymer system;
   c. measuring the fluorescence of the polymerizing polymer system; and
   d. comparing the measured fluorescence intensity to the extent of polymerization.

7. The method of claim 6, wherein the precursors are selected from the group consisting of: polyols, dianhydrides, diisocyanates and diamines and the curing agent is a diisocyanate or a diamine.

8. The method of claim 4, wherein the precursor comprises a diisocyanate having ether linkages.

9. A method of claim 6, wherein the label is selected from the group consisting of aromatic diisocyanates and diamine of conjugated aromatic compounds.

10. A method of claim 9, wherein the label is selected from the group consisting of naphthyl diamine, anthracenyl diamine, and naphthylene diisocyanate.

11. The method of claim 6 further comprising determining the fluorescence intensity per mole of the polymer compound when excited at the absorption maximum.

12. The method of claim 6 further comprising measuring the UV-VIS spectra of the polymerizing system.

13. The method of claim 12 further comprising deconvoluting the UV-VIS spectra to determine the concentration of the initial, intermediate and final polymerization products.

14. The method of claim 12 further comprising calibrating for concentration and thickness changes during polymerization using the UV-VIS spectra for said label.

15. The method of claim 13 further comprising determining the ratios of cross linker: branch point: linear-chain: chain-end: label.

16. The method of claim 13 further comprising modeling the overall fluorescence intensity as the sum of the fluorescence intensity of the initial, intermediate and final polymerization products.

17. The method of claim 16 further comprising constructing a curve relating fluorescence intensity with the overall extent of polymerization.

18. The method of claim 13 further comprising determining the soluble weight fraction from the concentration of the initial, intermediate and final polymerization products.

19. The method of claim 6 further comprising correcting for different reactivity ratios of the label and the curing agent.

* * * * *